US008753854B2

(12) United States Patent
Foody

(10) Patent No.: US 8,753,854 B2
(45) Date of Patent: **\*Jun. 17, 2014**

(54) METHOD FOR PRODUCING RENEWABLE FUELS

(71) Applicant: Iogen Bio-Products Corporation, Ottawa (CA)

(72) Inventor: Brian Foody, Ottawa (CA)

(73) Assignee: Iogen Corporation, Ontario (CA)

( \* ) Notice: Subject to any disclaimer, the term of this patent is extended or adjusted under 35 U.S.C. 154(b) by 0 days.

This patent is subject to a terminal disclaimer.

(21) Appl. No.: 13/722,522

(22) Filed: Dec. 20, 2012

(65) Prior Publication Data

US 2013/0164807 A1      Jun. 27, 2013

Related U.S. Application Data

(60) Provisional application No. 61/579,517, filed on Dec. 22, 2011.

(51) Int. Cl.
*C12P 5/00*       (2006.01)

(52) U.S. Cl.
USPC ........................................................ 435/166

(58) Field of Classification Search
CPC ............... C07C 5/02; C10L 3/10; C10L 3/08; C10L 3/101; C12P 5/00; Y02E 50/343; Y02E 50/13; Y02E 50/32
USPC ....................................................... 435/166
See application file for complete search history.

(56) References Cited

U.S. PATENT DOCUMENTS

| | | | |
|---|---|---|---|
| 3,105,811 A | 10/1963 | Engel | |
| 3,540,997 A | 11/1970 | Hahn et al. | |
| 4,372,856 A | 2/1983 | Morrison | |
| 7,931,888 B2 | 4/2011 | Drnevich et al. | |
| 2003/0111410 A1 | 6/2003 | Branson | |
| 2008/0159938 A1 | 7/2008 | Mauthner et al. | |
| 2008/0262701 A1\* | 10/2008 | Williams et al. | 701/103 |
| 2009/0313890 A1 | 12/2009 | Lopez et al. | |
| 2010/0015680 A1 | 1/2010 | Van Groenestijn et al. | |
| 2010/0047160 A1 | 2/2010 | Allam | |
| 2010/0158792 A1 | 6/2010 | Drnevich et al. | |
| 2010/0228067 A1 | 9/2010 | Peterson et al. | |
| 2011/0083997 A1 | 4/2011 | Silva et al. | |
| 2011/0158858 A1 | 6/2011 | Alves Ramalho Gomes | |
| 2011/0175032 A1 | 7/2011 | Gunther | |
| 2011/0226997 A1 | 9/2011 | Goruney et al. | |

FOREIGN PATENT DOCUMENTS

| | | |
|---|---|---|
| GB | 2466554 B | 6/2010 |
| WO | 03/051803 A1 | 6/2003 |
| WO | 2008044929 A1 | 4/2008 |
| WO | 2008/109122 A1 | 9/2008 |
| WO | 2009/126379 A1 | 10/2009 |
| WO | 2010/047815 A2 | 4/2010 |
| WO | 2010080407 A2 | 7/2010 |
| WO | 2011092136 A1 | 8/2011 |
| WO | 2012093041 A1 | 7/2012 |

OTHER PUBLICATIONS

Regalbuto, "An NSF perspective on next generation hydrocarbon biorefineries", Computers and Chemical Engineering 34 (2010) 1393-1396.
Serrano-Ruiz et al., "Catalytic routes for the conversion of biomass into liquid hydrocarbon transportation fuels", Energy & Environmental Science, 4 (2011) 83-99.
Börjesson et al., "Biogas as a resource-efficient vehicle fuel", Trends in Biotechnology, vol. 26, Issue 1 (2007) 7-13.
Cortright et al., "Hydrogen from catalytic reforming of biomass-derived hydrocarbons in liquid water", Nature, vol. 418 (2002) 964-67.
Cruz et al., "Petroleum Refinery Hydrogen Production Unit: Exergy [sic] and Production Cost Evaluation", International Journal of Thermodynamics, vol. 11, No. 4 (2008) 187-93.
Gruia, Practical Advances in Petroleum Processing, vol. 1, Ed. by Chang S. Hsu and Paul R. Robinson, Springer, New York, Chapter 8, "Recent Advances in Hydrocracking" (2006) 219-55.
Krich et al., Biomethane from Dairy Waste, "A Sourcebook for the Production and Use of Renewable Natural Gas in California" (Jul. 2005) 66-7 and 81-106.
Latvala "Using Biogas in the Production of Liquid Transport Fuels as Hydrogen Source", Second Nordic Biogas Conference, Malmo, Sweden (2008) 1-13.
Mezei, "Options for Upgrading Digester Biogas to Pipeline Quality", Flotech Services (2010) 1-15.
Milne et al., "Hydrogen from Biomass State of the Art and Research Challenges", National Renewable Energy Laboratory, A Report for the International Energy Agency Agreement on the Production and Utilization of Hydrogen Task 16, Hydrogen from Carbon-Containing Materials (2002) 1-78.
Najafpour et al., "Hydrogen as clean fuel via continuous fermentation by anaerobic photosynthetic bacteria, *Rhodospirillum rubrum*", African Journal of Biotechnology vol. 3, Issue 10 (2004) 503-7.
Robinson et al., Practical Advances in Petroleum Processing, vol. 1, Ed. by Chang S. Hsu and Paul R. Robinson, Springer, New York, Chapter 7, "Hydrotreating and Hydrocraking: Fundamentals" (2006) 177-218.

(Continued)

*Primary Examiner* — Karen Cochrane Carlson
*Assistant Examiner* — Jennifer M Tichy
(74) *Attorney, Agent, or Firm* — Fitzpatrick, Cella, Harper & Scinto

(57) ABSTRACT

According to the present invention, organic material is converted to biogas through anaerobic digestion and the biogas is purified to yield a combustible fluid feedstock comprising methane. A fuel production facility utilizes or arranges to utilize combustible fluid feedstock to generate renewable hydrogen that is used to hydrogenate crude oil derived hydrocarbons in a process to make transportation or heating fuel. The renewable hydrogen is combined with crude oil derived hydrocarbons that have been desulfurized under conditions to hydrogenate the liquid hydrocarbon with the renewable hydrogen or alternatively, the renewable hydrogen can be added to a reactor operated so as to simultaneously desulfurize and hydrogenate the hydrocarbons. The present invention enables a party to receive a renewable fuel credit for the transportation or heating fuel.

53 Claims, No Drawings

(56) References Cited

OTHER PUBLICATIONS

Schanbacher, "Anaerobic Digestion: Overview and Opportunities", Waste to Energy Workshop: Advances and Opportunities for Ohio's Livestock and Food Processing Industries, OARDC (Apr. 7, 2009) 1-28.

Shiga et al., "Large-Scale Hydrogen Production from Biogas", International Journal of Hydrogen Energy, vol. 23, No. 8 (1998) 631-40.

Spath et al., "Life Cycle Assessment of Hydrogen Production via Natural Gas Steam Reforming", NREL/TP-570-27637 (2000) 1-24.

"Clean and Renewable Energy from Pulp Mill Waste Using Microsludge and Anaerobic Digestion", Paradigm Environmental Technologies Inc. (2011) 1-2.

Clean Energy Strategies for Local Governments, 7.4 Landfill Methane Utilization (Dec. 10, 2008) 1-34.

U.S. Climate Change Technology Program—Technology Options for the Near and Long Term, Methane Emissions from Energy and Waste, "Conversion of Landfill Gas to Alternative Uses", section 4.1.2 (2003) 153-155.

Final Assessment Report "Landfill Biogas Recovery and Utilization at the Santo Andre Municipal Sanitary Landfill Santo Andre, Brazil", Prepared under: U.S. Environmental Protection Agency Landfill Methane Outreach Program (2008) 1-31.

"Natural Gas Processing: The Crucial Link Between Natural Gas Production and Its Transportation to Market", Energy Information Administration, Office of Oil and Gas (2006) 1-11.

Prospects for Hydrogen from Biomass, IEA Hydrogen Implementing Agreement, Annex 16, Subtask B, Final Report, (2006) 1-69.

* cited by examiner

METHOD FOR PRODUCING RENEWABLE FUELS

TECHNICAL FIELD

The present invention relates to a method for transforming waste organic material to produce a liquid transportation or heating fuel.

BACKGROUND

A majority of the energy used to provide fuels today is derived from fossil fuels, despite much effort and research on various alternative energy or non-fossil fuel options. The utilization of renewable biomass to produce fuel has been promoted by various governments, including the United States government through the Energy Independence and Security Act ("EISA") of 2007. Some of the purposes of the act are to increase the production of clean renewable fuels, to promote research on and deploy greenhouse gas ("GHG") capture and to reduce fossil fuels present in fuels. Notably, the act sets out a Renewable Fuels Standard ("RFS") with increasing annual targets for the renewable content of fuel sold or introduced into commerce in the United States.

The mandated annual targets of renewable content in fuel are implemented through an RFS that uses tradable credits (called Renewable Identification Numbers, referred to herein as "RINs") to track and manage the production, distribution and use of renewable fuels for transportation or other purposes. RINs can be likened to a currency used by obligated parties to certify compliance with mandated renewable fuel volumes. The U.S. Environmental Protection Agency ("EPA") is responsible for overseeing and enforcing blending mandates and developing regulations for the generation, trading and retirement of RINs.

Many approaches have been developed to use renewable biomass to produce transportation fuel or biofuels. Commercial biofuel production from carbohydrates currently employs starch or sugar cane as the feedstock. Production of ethanol from corn starch is widespread and ethanol from this source is considered a renewable fuel, and a first generation biofuel. It is often blended with gasoline, for example at levels of approximately 10% and the resulting blended gasoline can be considered to be a partially renewable transportation fuel. A given volume of such ethanol can have a RIN associated with it. This RIN is transferable to buyers of the ethanol or to producers of finished transportation fuel who use the ethanol to manufacture their finished transportation fuel.

However, starch and sugar cane are in high market demand as a food source for humans and animals, put upward pressure on food costs and thus are expensive and undesirable feedstocks for biofuel production. By contrast, agricultural residues and other non-food waste are inexpensive due to their wide availability and limited market value, and do not put pressure on food costs. Consequently, non-food feedstocks offer an attractive alternative to the starch and sugar cane feedstocks used to date as a source for biofuel production.

One of the leading approaches to producing liquid fuel from renewable feedstock involves the conversion of cellulosic biomass, a non-food source, to simple alcohols, such as ethanol, butanol and methanol. These alcohols can be used in a mixture with gasoline, or in their pure form, as liquid transportation fuel. Much attention and effort has been applied in recent years to the production of such liquid fuels from cellulosic biomass.

Cellulosic ethanol, in particular, has been the subject of significant research efforts. One of the leading technologies for producing ethanol from cellulosic biomass involves subjecting agricultural waste or other feedstocks containing cellulose to a series of chemical and biological treatments to produce glucose, which is then fermented to produce the ethanol. In particular, the process includes a chemical and/or heat pretreatment to improve the accessibility of the cellulose contained in the feedstock. This is followed by an enzymatic hydrolysis with cellulase enzymes to convert the cellulose to glucose. The glucose is fermented to ethanol by microorganisms, optionally in the presence of other sugars derived from the feedstock.

Other research efforts have been devoted to methanol and isobutanol production. One approach for producing methanol includes a thermochemical treatment of a feedstock to produce syngas, which is composed of hydrogen and carbon monoxide. The syngas is subsequently converted into the methanol, or other alcohols, with the aid of a chemical catalyst. Further research efforts have been directed to isobutanol production from renewable feedstocks by fermentation with yeast genetically engineered for such purpose.

Research and development efforts have also been directed towards the production of oils and diesels from renewable biomass. One technology includes a biomass catalytic cracking process that employs heat and a catalyst to convert biomass to a renewable crude oil with a relatively low oxygen content. Further, microorganisms have been used to ferment feedstock into carboxylic acids, which are then neutralized to form carboxylate salts. The carboxylate salts are then dewatered, dried and thermally converted to ketones, which are subsequently hydrogenated to form alcohols that can be refined into diesel or other fuels. Furthermore, oil can be produced from microalgae, which can then be converted to renewable diesel for ships or jet fuel. Moreover, other groups are investigating the production of biodiesel by yeast fermentation of feedstocks to an isoprenoid, which in turn is converted to diesel by a multi-step finishing process.

Other research efforts have been directed towards the production of gaseous hydrogen for direct use as a transportation fuel, which can be used in an internal combustion engine or a fuel cell. Such hydrogen can be produced by a variety of techniques. Some of the processes described in the literature include biomass pyrolysis or gasification and biological processes, such as bacterial fermentation and enzymatic hydrogen production.

At present, however, there is limited technical and economic infrastructure to support the widespread use of hydrogen directly as a transportation fuel. Although much effort has been devoted to using the gas as a transportation fuel, hydrogen is highly volatile and thus is dangerous to store and transport.

Yet another approach to generate a gaseous renewable fuel from waste feedstock includes anaerobic digestion of organic material derived from plants, vegetation, municipal waste, animal waste, animal byproducts, manure, sewage sludge, food waste, food processing waste, agricultural residues including corn stover and wheat straw and/or other biomass, hereinafter referred to collectively as "waste organic material". The combustible product of this digestion is referred to herein as "biogas" which may be produced by anaerobic digestion of any waste organic material. A main constituent of biogas is methane, although the gas also contains carbon dioxide and other components, depending on its source. The biogas may be produced by decomposing waste organic material under anaerobic conditions, such as in landfills.

There are commercial biogas applications that use biogas to produce electricity. In farming operations, biogas has been used to fuel engine-generators to produce electricity for onfarm use. In landfill operations, projects are underway to use biogas for electricity generation, either for on-site use or to sell to the grid. Other uses of biogas that have been described include transmitting biogas via pipeline to be combusted by an end user to fuel boilers, dryers, kilns, greenhouses, and other thermal applications (see http://www.epa.gov/statelocalclimate/documents/pdf/7.4_landfill_methane_utilization.pdf) Furthermore, in developing countries biogas is used for cooking.

The commercialization of processes for using biogas as a fuel has met limited success despite research and development efforts in this area. Although conventional gasoline powered automobiles can be run on biogas, they need to be retrofitted with compressed natural gas cylinders, which take up significant space in the trunk of a car or the bed of a pickup truck. To overcome the storage problems, automobiles need to be specially manufactured to accommodate the tanks under the body of the vehicle. Moreover, infrastructure required for biogas refueling is both costly and complex to implement and the demand for methane-fueled automobiles is relatively low. Thus, refueling stations are not always plentiful or conveniently located.

Although there have been numerous and wide ranging research efforts devoted to the implementation of renewable fuel production, the existing technologies for producing transportation or heating fuels with renewable content have been difficult to commercialize for various reasons. Despite business and legislative efforts to promote the production of renewable transportation or heating fuels, little progress has been made. There is therefore a need for a process that allows the energy in biomass to be captured and used in transportation fuel for conventional automobiles. Furthermore, there is a need to commercialize the use of biomass and other renewable resources as a source of energy, particularly for transportation or heating fuel. Technology that produces transportation or heating fuel from non-food biomass waste in a cost-effective manner would be desirable.

SUMMARY OF THE INVENTION

It is an object of the invention to provide an improved method for transforming waste organic material to produce a liquid transportation fuel.

The present invention provides a simple and cost effective method to utilize the energy in waste organic material to increase the renewable energy content of transportation fuels used commercially in conventional automobiles. The invention provides a method for using renewable biomass to replace or reduce the quantity of fossil derived energy present in transportation and heating fuels.

It is a further object of this invention to provide an improved method for transforming waste organic material to produce a heating fuel, such as home heating fuel and commercial heating fuel, heating fuels made from naphtha, liquid petroleum gas, kerosene, or other heating fuels that can be made in accordance with the process of the invention.

The present invention provides a renewable fuel or a fuel having renewable content that is produced from renewable biomass. Renewable fuel or fuel having renewable content is produced from a renewable biomass and is used to replace or reduce the quantity of fossil fuel present in a transportation fuel or heating fuel. The replacement or reduction of fossil fuel is based on an aggregate of fossil fuels on a macro level or it can be based on the actual fuel produced or both. The fuel may be a partially renewable fuel, meaning that it is produced by co-processing a feedstock derived from renewable biomass and non-renewable feedstocks. Preferably, the fuel is a transportation fuel.

The fuel produced by the invention, including transportation and heating fuel, is made by a process that comprises a step of hydrogenation. According to one aspect of the present invention, waste organic material is converted to crude biogas through anaerobic digestion and the biogas is purified to yield a combustible fluid feedstock comprising predominantly methane; a fuel production facility utilizes or arranges to utilize combustible fluid feedstock to generate renewably sourced hydrogen that is used to hydrogenate crude oil derived hydrocarbons to make liquid transportation or heating fuel products that contain renewable content. Preferably, this renewably sourced hydrogen is combined with crude oil derived hydrocarbons that have been desulfurized under conditions to hydrogenate the liquid hydrocarbon with the renewable hydrogen or alternatively, the renewably sourced hydrogen can be added to a reactor operated so as to simultaneously desulfurize and hydrogenate the hydrocarbons, preferably using non-renewable hydrogen to desulfurize.

The invention further provides a means for satisfying renewable fuel targets or mandates established by governments, including legislation and regulations for transportation fuel or heating fuel sold or introduced into commerce in the United States. The invention also provides a means for satisfying low carbon fuel standards established by governments including states within the United States such as California. Transportation or heating fuel produced by the process of the present invention or intermediates produced thereunder are believed to be eligible for generation of RINs or tradable certificates.

The invention can be considered as a method of producing a fuel, preferably a liquid transportation fuel, comprising the steps of (i) producing renewable hydrogen from a combustible fluid feedstock, preferably a biogas derived combustible fluid feedstock; (ii) combining the renewable hydrogen with a desulfurized, crude oil derived liquid hydrocarbon in a reactor under conditions to hydrogenate the liquid hydrocarbon with the renewable hydrogen; (iii) producing a fuel that has associated with it lower greenhouse gas emissions compared to baseline emissions for gasoline, preferably at least 20% lower than baseline emissions for gasoline, more preferably at least 30%, 40% 50% lower than baseline emissions for gasoline; and optionally (iv) receiving a renewable fuel credit as described herein and known in the art. Alternatively, an amount of renewable hydrogen can be combined with a crude oil derived liquid hydrocarbon and an additional effective amount of hydrogen of sufficient quantity to desulfurize the crude oil derived liquid hydrocarbon in a reactor under conditions to simultaneously desulfurize and hydrogenate the crude oil derived liquid hydrocarbon, where preferably the amount of hydrogen that becomes bonded to the crude oil derived liquid hydrocarbon is greater than or equal to two thirds of the amount of renewable hydrogen.

According to a further aspect, the present invention provides a method of transforming waste organic material to produce a liquid transportation or heating fuel comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of combustible fluid feedstock from step (b) or (c) to apparatus for delivering a combustible fluid feedstock to a fuel production facility; (e) withdrawing for use at a fuel production facility a second amount of combustible fluid feedstock approximately equal to the first amount of combustible fluid feedstock; (f) processing at the fuel production facility the second amount of combustible fluid feedstock to produce renewable hydrogen; and (g) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

In another aspect, the present invention provides a method of producing a transportation or heating fuel comprising: (a) causing a first amount of combustible fluid feedstock to be introduced to apparatus for delivering a combustible fluid feedstock to a fuel production facility, the first amount of combustible fluid feedstock being derived from a crude biogas that was generated by anaerobic digestion of waste organic material and from which impurities were removed following collection from a biogas production facility; (b) withdrawing for use at a fuel production facility, a second amount of combustible fluid feedstock approximately equal to the first amount of combustible fluid feedstock; (c) processing at the fuel production facility the second amount of combustible fluid feedstock to produce renewable hydrogen; and (d) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

According to a further aspect, there is provided a method of producing a combustible fluid feedstock for use in producing a transportation or heating fuel, the method comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of combustible fluid feedstock from step (b) or (c) to apparatus for delivering a combustible fluid feedstock to fuel production facility; and (e) causing a fuel production facility to use combustible fluid feedstock in a process for producing transportation or heating fuel, the process comprising: (i) withdrawing for use at a fuel production facility a second amount of combustible fluid feedstock from the apparatus approximately equal to the first amount of combustible fluid feedstock; (ii) processing the second amount of combustible fluid feedstock to produce renewable hydrogen; and (iii) combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

According to another aspect, the present invention further provides a method of transforming waste organic material to produce a liquid transportation or heating fuel comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of the combustible fluid feedstock from step (b) or (c) to apparatus for delivering a combustible fluid feedstock to fuel production facility; (e) withdrawing for use at a fuel production facility a second amount of combustible fluid feedstock approximately equal in energy content to the first amount of combustible fluid feedstock; (f) processing at the fuel production facility the second amount of combustible fluid feedstock to produce a third amount of renewable hydrogen; and (g) producing a fourth amount of liquid transportation or heating fuel by a process that comprises combining the third amount of renewable hydrogen derived from the second amount of combustible fluid feedstock with a crude oil derived liquid hydrocarbon and an additional effective amount of hydrogen of sufficient quantity to desulfurize the crude oil derived liquid hydrocarbon, wherein step (g) is carried out in a reactor under conditions to simultaneously desulfurize and hydrogenate the crude oil derived liquid hydrocarbon; and wherein the amount of the hydrogen that becomes bonded to the crude oil derived liquid hydrocarbon in step (g) is greater than or equal to two thirds of the third amount of renewable hydrogen.

In another aspect, the invention provides a method of producing a transportation or heating fuel comprising: (a) causing a first amount of combustible fluid feedstock to be introduced to apparatus for delivering combustible fluid feedstock to a fuel production facility, the first amount of combustible fluid feedstock being derived from a crude biogas that was generated by anaerobic digestion of waste organic material and from which impurities were removed following collection from a biogas production facility; (b) withdrawing for use at a fuel production facility, a second amount of combustible fluid feedstock approximately equal to the first amount of combustible fluid feedstock; (c) processing at the fuel production facility the second amount of combustible fluid feedstock to produce a third amount of renewable hydrogen; (d) producing a fourth amount of liquid transportation or heating fuel by a process that comprises combining the third amount of renewable hydrogen derived from the second amount of combustible fluid feedstock with a crude oil derived liquid hydrocarbon and an additional effective amount of hydrogen of sufficient quantity to desulfurize the crude oil derived liquid hydrocarbon, wherein step (d) is carried out in a reactor under conditions to simultaneously desulfurize and hydrogenate the crude oil derived liquid hydrocarbon; and wherein the amount of hydrogen that becomes bonded to the crude oil derived liquid hydrocarbon is greater than or equal to two thirds of the third amount of renewable hydrogen.

In another aspect, there is further provided a method of producing a combustible fluid feedstock for use in producing a transportation or heating fuel, the method comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of combustible fluid feedstock from step (b) or (c) to apparatus for delivering a combustible fluid feedstock to fuel production facility; and (e) causing a fuel production facility to use combustible fluid feedstock in a process for producing transportation or heating fuel, the process comprising: (i) withdrawing for use at a fuel production facility a second amount of combustible fluid feedstock from the apparatus approximately equal to the first amount of combustible fluid feedstock; (ii) processing the second amount of combustible fluid feedstock to produce a third amount of renewable hydrogen; and (iii) producing a fourth amount of liquid transportation or heating fuel by a process that comprises combining the third amount of renewable hydrogen derived from the second amount of combustible fluid feedstock with a crude oil derived liquid hydrocarbon and an additional effective amount of hydrogen of sufficient quantity to desulfurize the crude oil derived liquid hydrocarbon, wherein step (iii) is carried out in a reactor under conditions to simultaneously desulfurize and hydrogenate the crude oil derived liquid hydrocarbon; and wherein the amount of hydrogen that becomes bonded to the crude oil derived liquid hydrocarbon is greater than or equal to two thirds of the third amount of renewable hydrogen.

In another aspect, the invention provides a method of producing a transportation or heating fuel comprising: (a) causing a first amount of combustible fluid feedstock to be introduced to apparatus for delivering combustible fluid feedstock to a fuel production facility, the first amount of combustible fluid feedstock being derived from a crude biogas that was generated by anaerobic digestion of waste organic material and from which impurities were removed following collection from a biogas production facility; (b) withdrawing for use at a fuel production facility, a second amount of combustible fluid feedstock approximately equal to the first amount of combustible fluid feedstock; (c) processing at the fuel production facility the second amount of combustible fluid feedstock to produce a third amount of renewable hydrogen; (d) producing a fourth amount of liquid transportation or heating fuel by a process comprising combining the third amount of renewable hydrogen derived from the second amount of combustible fluid feedstock with a crude oil derived liquid hydrocarbon in a reactor under conditions to simultaneously desulfurize and hydrogenate the crude oil derived liquid hydrocarbon.

In another aspect, there is further provided a method of producing a combustible fluid feedstock for use in producing a transportation or heating fuel, the method comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of combustible fluid feedstock from step (b) or (c) to apparatus for delivering a combustible fluid feedstock to fuel production facility; and (e) causing a fuel production facility to use combustible fluid feedstock in a process for producing transportation or heating fuel, the process comprising: (i) withdrawing for use at a fuel production facility a second amount of combustible fluid feedstock from the apparatus approximately equal to the first amount of combustible fluid feedstock; (ii) processing the second amount of combustible fluid feedstock to produce a third amount of renewable hydrogen; and (iii) producing a fourth amount of liquid transportation or heating fuel by a process that comprises combining the third amount of renewable hydrogen derived from the second amount of combustible fluid feedstock with a crude oil derived liquid hydrocarbon, wherein step (iii) is carried out in a reactor under conditions to simultaneously desulfurize and hydrogenate the crude oil derived liquid hydrocarbon.

In any of the foregoing aspects of the invention, a renewable fuel credit may be associated with the combustible fluid feedstock, the renewable hydrogen, the liquid transportation or heating fuel, or a combination thereof. Preferably, a renewable fuel credit is associated with a liquid transportation or heating fuel. More preferably, a renewable fuel credit is associated with the liquid transportation fuel.

In a further aspect, the present invention provides a method that comprises generating numerical information to support a renewable fuel credit associated with a product produced in accordance with the method of the invention, which product is selected from (i) the combustible fluid feedstock derived from biogas; (ii) the renewable hydrogen; (iii) the transportation or heating fuel comprising renewable hydrogen; and (iv) the crude biogas.

According to another aspect of the invention, there is provided a method of transforming waste organic material to produce a liquid transportation or heating fuel comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of the combustible fluid feedstock from step (b) or (c) to apparatus for delivering a combustible fluid feedstock to fuel production facility; (e) generating numerical information relating to the first amount of combustible fluid feedstock or crude biogas comprising information representing at least 3 parameters selected from: (i) the type of renewable fuel that it is; (ii) year in which the combustible fluid feedstock was produced; (iii) a registration number associated with the producer or importer of the combustible fluid feedstock; and (iv) a serial number associated with a batch of the combustible fluid feedstock; and (f) withdrawing for use at a fuel production facility a second amount of combustible fluid feedstock approximately equal to the first amount of combustible fluid feedstock; (g) processing at the fuel production facility the second amount of combustible fluid feedstock to produce renewable hydrogen; and (h) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

In another aspect of the invention, there is provided a method of producing a transportation or heating fuel comprising: (a) causing a first amount of combustible fluid feedstock to be introduced to apparatus for delivering a combustible fluid feedstock to a fuel production facility, the first amount of combustible fluid feedstock being derived from a crude biogas that was generated by anaerobic digestion and from which impurities were removed following collection from a biogas production facility; (b) withdrawing for use at a fuel production facility, a second amount of combustible fluid feedstock approximately equal to the first amount of combustible fluid feedstock; (c) processing at the fuel production facility the second amount of combustible fluid feedstock to produce renewable hydrogen; (d) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen; and (e) receiving and storing numerical information relating to the first amount of combustible fluid feedstock or crude biogas comprising information representing at least 3 parameters selected from: (i) the type of renewable fuel that it is; (ii) year in which the combustible fluid feedstock was produced; (iii) a registration number associated with the producer or importer of the combustible fluid feedstock; and (iv) serial number associated with a batch of the combustible fluid feedstock.

According to a further aspect of the invention, there is provided a method of producing a combustible fluid feedstock for use in producing a transportation or heating fuel, the method comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) generating numerical information relating to the first amount of combustible fluid feedstock or crude biogas comprising information representing at least 3 parameters selected from: (i) the type of renewable fuel that it is; (ii) year in which the combustible fluid feedstock was produced; (iii) a registration number associated with the producer or importer of the combustible fluid feedstock; and (iv) a serial number associated with a batch of the combustible fluid feedstock; and (e) introducing a first amount of combustible fluid feedstock from step (b) or (c) to apparatus for delivering a combustible fluid feedstock to a fuel production facility; and (f) causing a fuel production facility to use combustible fluid feedstock in a process for producing transportation or heating fuel, the process comprising: (i') withdrawing for use at a fuel production facility a second amount of combustible fluid feedstock from the apparatus approximately equal to the first amount of combustible fluid feedstock; (ii') processing the second amount of combustible fluid feedstock to produce renewable hydrogen; and (iii') combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

In another aspect, the present invention further provides a method of producing a transportation or heating fuel comprising: (a) receiving combustible fluid feedstock in accordance with an arrangement with a producer or supplier of combustible fluid feedstock derived from crude biogas, the arrangement relating to the use of combustible fluid feedstock in a process for producing liquid transportation or heating fuel; (b) producing renewable hydrogen from the received combustible fluid feedstock; (c) producing liquid transportation or heating fuel in a process that comprises combining renewable hydrogen with crude oil derived liquid hydrocarbons under conditions to hydrogenate the liquid hydrocarbons; (d) generating or receiving numerical information relating to a product selected from (i) combustible fluid feedstock derived from biogas; (ii) renewable hydrogen; (iii) a transportation or heating fuel comprising renewable hydrogen; and (iv) crude biogas, the numerical information comprising information representing at least 3 parameters selected from: (i') the type of product that is made by a producer or importer of the product; (ii') year in which the product was produced; (iii') a registration number associated with the producer or importer of the product; and (iv') a serial number associated with a batch of the product; and (e) providing the numerical information generated or received in step (d) from a producer or purchaser of the product to a government regulatory agency.

In another aspect, the present invention provides a method of producing a combustible fluid feedstock for use in producing a transportation or heating fuel, the method comprising: (a) producing a combustible fluid feedstock by a process comprising: (i) converting waste organic material to crude biogas using microorganisms; (ii) collecting an amount of crude biogas using an apparatus; and (ii) removing impurities from the crude biogas to yield a combustible fluid feedstock; (b) arranging for a fuel production facility to receive combustible fluid feedstock to use in a process for making liquid transportation or heating fuel, wherein the process comprises combining renewable hydrogen derived from the combustible fluid feedstock with crude oil derived liquid hydrocarbons under conditions to hydrogenate the liquid hydrocarbons; (c) generating numerical information relating to the combustible fluid feedstock or crude biogas, the information comprising information representing at least 3 parameters selected from: (i') the type of renewable fuel that it is; (ii') year in which the combustible fluid feedstock was produced; (iii') a registration number associated with the producer or importer of the combustible fluid feedstock; and (iv') a serial number associated with a batch of the combustible fluid feedstock; and (d) providing the numerical information relating to the combustible fluid feedstock or crude biogas to a government regulatory agency and to the fuel production facility in step (b).

According to yet a further aspect of the invention, there is provided a method for generating a renewable fuel credit associated with biogas produced from waste organic material, the method comprising: (a) producing biogas derived combustible fluid feedstock from biogas; (b) arranging for a fuel production facility to buy combustible fluid feedstock to make renewable hydrogen for use in a process for making liquid transportation or heating fuel, wherein the process comprises combining renewable hydrogen with crude oil derived liquid hydrocarbons to hydrogenate the liquid hydrocarbons; (c) generating a RIN associated with the biogas; (d) introducing a first amount of the biogas derived combustible fluid feedstock to apparatus for delivering a combustible fluid feedstock to fuel production facility; and (e) transferring a RIN associated with biogas to a purchaser of the biogas.

In a further aspect of the invention, there is provided a method of transforming waste organic material to produce a liquid transportation or heating fuel comprising: (a) subjecting waste organic material to anaerobic digestion by microorganisms in a biogas production facility that incorporates apparatus to collect the microbially generated biogas; (b) collecting an amount of crude biogas from the biogas production facility; (c) removing impurities from the crude biogas to yield a combustible fluid feedstock; (d) introducing a first amount of the combustible fluid feedstock from step (b) or (c) to apparatus for delivering a combustible fluid feedstock to fuel production facility; (e) generating or receiving numerical information relating to a product selected from (i) combustible fluid feedstock derived from crude biogas; (ii) renewable hydrogen; (iii) a transportation or heating fuel comprising renewable hydrogen; or (iv) crude biogas, the numerical information comprising information representing at least 3 parameters selected from: (i') the type of product that is made by the producer or importer of the product; (ii') year in which the product was produced; (iii') a registration number associated with the producer or importer of the product; and (iv') a serial number associated with a batch of the product; (f) withdrawing for use at a fuel production facility a second amount of combustible fluid feedstock approximately equal to the first amount of combustible fluid feedstock; (g) processing at the fuel production facility the second amount of combustible fluid feedstock to produce renewable hydrogen; (h) producing a third amount of liquid transportation or heating fuel by a process that comprises combining renewable hydrogen derived from the second amount of combustible fluid feedstock with a crude oil derived liquid hydrocarbon; and (i) providing the numerical information generated or received in step (e) to a government regulatory agency.

According to a further aspect of the invention, there is provided method of producing a transportation or heating fuel comprising: (a) causing a first amount of combustible fluid feedstock to be introduced to apparatus capable of delivering a combustible fluid feedstock to a fuel production facility, the first amount of combustible fluid feedstock being derived from a crude biogas from which impurities were removed following collection from a biogas production facility; (b) generating or receiving numerical information relating to a product selected from (i) combustible fluid feedstock derived from crude biogas; (ii) renewable hydrogen; (iii) a transportation or heating fuel comprising renewable hydrogen; and (iv) crude biogas, the numerical information comprising information representing at least 3 parameters selected from: (i') the type of product that is made by a producer or importer of the product; (ii') year in which the product was produced; (iii') a registration number associated with the producer or importer of the product; and (iv') a serial number associated with a batch of the product; (c) withdrawing for use at a fuel production facility, a second amount of combustible fluid feedstock approximately equal to the first amount of combustible fluid feedstock; (d) processing at the fuel production facility the second amount of combustible fluid feedstock to produce renewable hydrogen; (e) producing a third amount of liquid transportation or heating fuel by a process that comprises combining renewable hydrogen derived from the second amount of combustible fluid feedstock with a crude oil derived liquid hydrocarbon; and (f) providing numerical information generated or received in step (b) to a government regulatory agency.

According to another aspect of the invention, there is provided a method of producing a combustible fluid feedstock for use in producing a partially renewable transportation or heating fuel, the method comprising: (a) producing or receiving combustible fluid feedstock derived from biogas that has been produced from waste organic material; (b) introducing a first amount of the combustible fluid feedstock from step (a) to apparatus for delivering a combustible fluid feedstock to a fuel production facility; and (c) causing a fuel production facility to use combustible fluid feedstock in a process that produces transportation or heating fuel from a crude oil derived hydrocarbon, the process comprising: withdrawing a second amount of combustible fluid feedstock from the apparatus approximately equal to the first amount of combustible fluid feedstock; (d) generating numerical information relating to the first amount of combustible fluid feedstock comprising information representing at least 3 parameters selected from: (i) the type of renewable fuel that it is; (ii) year in which the combustible fluid feedstock was produced; (iii) a registration number associated with the producer or importer of the combustible fluid feedstock; and (iv) a serial number associated with a batch of the combustible fluid feedstock; and (e) providing the numerical information relating to the first amount of combustible fluid to a government regulatory agency and a purchaser of the combustible fluid feedstock.

According to any one of the foregoing aspects of the invention, the transportation or heating fuel produced by the process of the invention may be selected from gasoline, diesel, heating oil and jet fuel.

According to an embodiment of any one of the above aspects of the invention, the fuel produced by the invention is a transportation fuel. The fuel production facility is preferably a transportation fuel production facility.

According to any one of the foregoing aspects of the invention, the fuel produced by the invention may be heating fuel such as heating oil.

In a non-limiting embodiment of the invention, hydrogen atoms from the combustible fluid feedstock become incorporated into the final transportation fuel or heating fuel. Preferably, the transportation or heating fuel is, or qualifies as, renewable or partially renewable.

According to an embodiment of any one of the above aspects of the invention, the biogas production facility is a landfill, a waste treatment facility or a manure digestion facility.

According to those aspects of the invention that comprise combining renewable hydrogen with a desulfurized, crude oil derived liquid hydrocarbon, the reactor is preferably a hydrogenation reactor. In one embodiment of the invention, the hydrogenation reactor is a hydrocracker.

In those aspects of the invention in which the crude oil derived liquid hydrocarbon is simultaneously desulfurized and hydrogenated, the reactor is preferably one that carries out both hydrotreating and hydrocracking In those aspects of the invention in which an additional effective amount of hydrogen is used to desulfurize, such hydrogen is preferably non-renewable.

DETAILED DESCRIPTION

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting.

Source of Biogas

Any source material containing waste organic material can be used in the process of the invention to produce biogas. Waste organic material includes, but is not limited to, landfill waste, agricultural waste including manure and crop waste products, sewage sludge, food waste, yard waste, industrial waste, animal waste material, for example, slaughterhouse waste and fish waste, fats, oils and grease from restaurants, or a combination thereof. By the term "organic material", it is meant any non-fossil fuel substrate that can be converted into biogas, most preferably by anaerobic digestion using microorganisms.

In one exemplary embodiment of the invention, the organic material includes, but is not limited to biomass, such as (i) animal waste material and animal byproducts; (ii) separated yard waste or food waste, including recycled cooking and trap grease; and (iii) landfill waste, including, but not limited to, food and yard waste. The organic material in the landfill waste, including, but not limited to, food and yard waste, may or may not be intermixed with non-organic components of landfill material.

Biogas Production and Collection

According to the present invention, the waste organic material is subjected to anaerobic digestion in a biogas production facility to generate biogas. "Anaerobic digestion" is the biological breakdown of organic material by microorganisms under low oxygen conditions, or in the absence of oxygen, to produce a gas comprising methane, referred to herein as biogas. As used herein, the term encompasses any method for microbially digesting waste organic matter under anaerobic conditions. The digestion may or may not be contained within an anaerobic digester, as described further below. As known to those skilled in the art, anaerobic digestion generally involves the decomposition of waste organic material, including carbohydrates, fats and proteins therein, into simple sugars and glycerol. These compounds are then converted to acids, which are then converted into methane by methanogenic bacteria or other microorganisms.

The biogas production facility is an operation that produces biogas either as a target product or as a co-product and includes an agricultural, municipal or industrial operation.

This includes, without limitation, a landfill, a facility containing anaerobic digesters, a waste treatment facility, such as a sewage treatment facility, and a manure digestion facility, such as a facility located on a farm or processing materials collected from farms. Biogas may be provided through importation.

The biogas utilized in the present invention is optionally derived from landfill waste. Landfill biogas may be produced by organic material decomposing under anaerobic conditions in a landfill. The waste is covered and mechanically compressed by the weight of the material that is deposited from above. This material prevents oxygen exposure thus allowing anaerobic microbes to thrive. By appropriately engineering a collection system at the landfill site, the resultant biogas is captured. Biogas can also be produced from organic material that is separated from waste that otherwise goes to landfills. According to further embodiments of the invention, the biogas production site contains an anaerobic digester for digesting the waste.

An anaerobic digester is a tank, or other contained volume, such as a covered lagoon, designed to facilitate the breakdown of organic material or biomass by microorganisms under anaerobic or low oxygen conditions. The anaerobic digestion may be carried out in one or multiple anaerobic digesters. An anaerobic digester utilized in accordance with the invention may be designed and/or operated in a number of configurations including batch or continuous, mesophilic or thermophilic temperature ranges, and low, medium or high rates. The rate refers to the chemical oxygen demand (COD) feed rate to the unit, which is a rate measurement based on the organic compounds present in the feed. In practice, the choice of configuration will depend on a number of factors. These may include consideration of the nature of the organic material or biomass to be treated and/or the level of treatment desired. Other factors that may be considered in the configuration choice include operating parameters such as residence time, temperature, pH and the nutrients supplied to a digester.

In some embodiments of the invention, the biogas production facility is a centralized facility that receives organic material that is transported to the facility from different sources. The biogas production facility can be located at a fuel production facility, which is described hereinafter.

Crude biogas is collected from the biogas production facility by an apparatus designed for such purpose. Non-limiting examples of apparatus to collect microbially generated biogas that may be used in accordance with the invention include apparatus disclosed in U.S. Pat. Nos. 7,951,296 and 7,972,082 and WO 2010/051622, each of which is incorporated herein by reference.

Crude biogas from landfills may be collected through extraction wells. The crude biogas can also be extracted through horizontal trenches. The crude biogas may then be extracted and piped to a main collection header. The main collection header can be connected to a leachate collection system. A blower may be needed to pull the gas from the collection wells to the collection header and further downstream.

Alternatively, an existing landfill biogas vent can be converted to a vertical well. The density of the wells within the landfill generally varies, depending on the composition of the landfill waste. As set out above, the landfill site may contain an anaerobic digester, in which case the apparatus collects biogas originating from the anaerobic digester.

Biogas can be withdrawn from a digester by a pipe or other similar apparatus for removing the biogas from the digester. The pipe or other similar apparatus may be placed at the top region of the digester to collect the biogas, or any other suitable location to withdraw or remove the biogas from the digester.

Optionally, the biogas is stored prior to use, purification or transport.

Biogas Purification

Apart from the desired methane, the crude biogas will typically contain one or more impurities such as carbon dioxide, hydrogen sulfide, water, oxygen, nitrogen and halogenated compounds. The impurities in the crude biogas can be removed by any suitable method, or combination of methods to yield relatively purified combustible fluid feedstock. The crude biogas can be purified to any degree, including, but not limited to, the extent required to meet pipeline specifications. Although typically in gas form, the combustible fluid feedstock can be a liquid or a gas. In a preferred embodiment of the invention, at least carbon dioxide is removed from the crude biogas, although other impurities can optionally be removed as well.

Carbon dioxide removal from the crude biogas may be carried out by scrubbing techniques such as water or polyethylene glycol scrubbing, which involve flowing biogas through a column with a water or polyethylene glycol solution flowing counter-current to the biogas. Carbon dioxide is removed from the crude biogas by these techniques since it is more soluble in water or polyethylene glycol than methane.

A further technique for carbon dioxide removal from the crude biogas is pressure swing absorption, which utilizes adsorptive materials, such as zeolites and activated carbon that preferentially adsorb carbon dioxide at high pressure. When the pressure is released, the carbon dioxide desorbs.

Membrane separation is another technique that can be used to remove carbon dioxide from the crude biogas. Membrane separation may include high pressure gas separation or gas-liquid absorption membranes.

According to further embodiments of the invention, removal of hydrogen sulfide from the crude biogas is carried out by bacteria, such as chemotrophic thiobacteria that are capable of oxidizing hydrogen sulfide and using carbon dioxide as a carbon source. Bacterial removal of hydrogen sulfide may be carried out in an anaerobic digester or a storage tank. The addition of oxygen into a digester or storage tank promotes the growth of indigenous thiobacteria. In further exemplary embodiments, removal of hydrogen sulfide by bacteria is combined with water scrubbing. Another method for removing hydrogen sulfide is the addition of iron chloride to an anaerobic digester. The iron chloride reacts with hydrogen sulfide that is produced to form iron sulfide salt. Other non-limiting examples of techniques that can be utilized to remove hydrogen sulfide include the addition of iron oxide to a digester, which reacts with hydrogen sulfide to produce iron sulfide, pressure swing absorption, water scrubbing, polyethylene glycol scrubbing and sodium hydroxide scrubbing.

Halogenated hydrocarbons can be removed by contacting the biogas with activated carbon. Oxygen and nitrogen impurities can be removed by membranes or pressure swing adsorption.

Combustible fluid feedstock is a combustible fluid that predominantly comprises methane. The fluid is typically a gas but may be a liquid. In certain embodiments of the invention, the combustible fluid feedstock comprises predominantly methane and may further comprise other volatile combustible hydrocarbons. Combustible fluid feedstock may be derived from biogas, either crude or purified to any degree.

Transport of Combustible Fluid Feedstock

After generation, the combustible fluid feedstock is introduced to an apparatus for delivering combustible fluid feedstock to a fuel production facility. In a preferred embodiment, such apparatus will be a pipeline, such as a natural gas pipeline or a biogas dedicated pipeline. Alternatively, the apparatus may be a container for transporting the combustible fluid feedstock by rail, trucking or shipping, or any other commercial distribution system. A combustible fluid feedstock may be transported in gaseous or liquid form. Combustible fluid feedstock derived from biogas is introduced into the apparatus described above and transported to a fuel production facility.

Combustible fluid feedstock is supplied or transported to a fuel production facility for use in making liquid transportation fuels. As is well-understood in the art, however, combustible fluid feedstock may also be supplied or transported to fuel production facilities for making fuels for other uses, such as heating fuels, in conformity with the processes described herein. By the term "fuel production facility", it is meant any processing plant or plants where crude oil or crude oil derived hydrocarbons are processed and refined into more useful products that include fuel, liquid transportation fuel, fuel intermediates, fuel components, or any combination thereof. Non-limiting examples include, but are not limited to, gasoline, diesel fuel, kerosene, fuels made from naphtha, fuel oils and liquefied petroleum gas. By the term "transportation fuel production facility", it is meant any processing plant or plants where crude oil or crude oil derived hydrocarbons are processed and refined into liquid transportation fuel, intermediates or components thereof, or any combination of the foregoing. The crude oil may be derived from oil reservoirs, such as hydrocarbons found within rock formations, oil sands or oil shale.

Combustible fluid feedstock is supplied or transported to the fuel production facility. In some embodiments of the invention, the apparatus for transport is a commercial distribution system, such as a natural gas pipeline, in which case biogas derived combustible fluid feedstock may become intermixed with methane that originates from fossil fuel sources (natural gas). In such embodiments of the invention, the combustible fluid feedstock that is withdrawn to make renewable hydrogen and transportation or heating fuel therefrom may comprise methane from biogas, methane from natural gas or mixtures thereof.

The apparatus for delivering combustible fluid feedstock may be integral or connected with the apparatus to collect the biogas in the biogas production facility. Alternatively, the apparatus for delivering combustible fluid feedstock and the apparatus to collect the biogas are separate, unconnected units. The apparatus for delivering a combustible fluid feedstock to a fuel production facility delivers, or is capable of delivering, combustible fluid feedstock to one or more fuel production facilities. It should also be appreciated that the biogas production facility could be located on-site or in close proximity to the fuel production facility. Combustible fluid feedstock is withdrawn from apparatus at a fuel production facility and then processed to produce renewable hydrogen.

Renewable Hydrogen Production from Biogas

Renewable hydrogen is hydrogen made using renewably sourced combustible fluid feedstock. This includes hydrogen made using any of the following, or any combination of the following: (a) combustible fluid feedstock purified or derived directly from biogas; and (b) combustible fluid feedstock sourced by the steps of (i) causing (as described herein) a first amount of combustible fluid feedstock derived from crude biogas to be introduced into apparatus for delivering combustible fluid feedstock to processing facilities; and (ii) withdrawing at the destination a second amount of combustible fluid feedstock approximately equal in energy content to the first amount of combustible fluid feedstock. Renewable hydrogen includes hydrogen sourced from (i) biogas derived from anaerobic digestion; (ii) methane, including natural gas or fossil fuel derived methane which qualifies under applicable laws and regulations to be treated as renewably derived biogas; or (iii) any combination of (i) or (ii).

Renewable hydrogen production from combustible fluid feedstock may be carried out by any suitable means known to those of skill in the art. Technologies that can be utilized in accordance with the present invention for producing renewable hydrogen from methane include, but are not limited to, autothermal reforming ("ATR") and steam methane reforming ("SMR") and additionally water gas shift reactions or other like technologies as known to those skilled in the art. Both ATR and SMR methods operate by exposing the combustible fluid feedstock or methane therein to a catalyst at high temperature and pressure to produce syngas, which is renewable hydrogen and carbon monoxide. The carbon monoxide generated by either method may be generally further reacted with water in a water gas shift reaction to form carbon dioxide and renewable hydrogen. SMR converts the methane into renewable hydrogen and carbon monoxide without oxygen. The carbon monoxide reacts further to produce more renewable hydrogen in the water gas shift reaction. The relevant equations are as follows:

$$CH_4 + H_2O \rightarrow CO + 3H_2$$

$$CO + H_2O \rightarrow CO_2 + H_2$$

Without being limiting, conventional steam reforming plants may operate at pressures between 200 and 600 psi with outlet temperatures in the range of 815 to 925° C.

ATR uses oxygen and carbon dioxide or steam in a reaction with methane to form syngas and water. The reaction may take place in a single chamber where the methane is partially oxidized. The reaction is exothermic due to the oxidation. The reactions can be described in the following equations, using $CO_2$:

$$2CH_4 + O_2 + CO_2 \rightarrow 3H_2 + 3CO + H_2O$$

and using steam:

$$4CH_4 + O_2 + 2H_2O \rightarrow 10H_2 + 4CO.$$

A significant difference between SMR and ATR is that SMR uses no oxygen.

SMR and ATR are carried out in any suitable device or devices for producing renewable hydrogen from a combustible fluid feedstock and include devices and operations that are known or used in the art for such purposes. The steam reforming operation may be situated in the fuel production facility or the operation may be a separate plant located off-site.

It is preferred that the renewable hydrogen produced by SMR or ATR be purified to remove one or more non-hydrogen components. The renewable hydrogen may be purified by methods known to those skilled in the art, such as liquid absorption system for carbon dioxide removal or a pressure swing absorption operation to produce a purified renewable hydrogen product.

Production of Fuel

After production, the renewable hydrogen is used in a process to produce a liquid transportation or heating fuel. The renewable hydrogen is combined with a crude oil derived liquid hydrocarbon so that it becomes incorporated into the hydrocarbon and ultimately is part of the liquid transportation or heating fuel that is the product of the fuel production facility. By the term "crude oil derived liquid hydrocarbon", it is meant any carbon-containing material derived from crude oil that is liquid at standard ambient temperature and pressure. Crude oil includes liquid, gaseous and solid carbon-containing material from geologic formations, including oil reservoirs, such as hydrocarbons found within rock formations, oil sands or oil shale. Advantageously, since the hydrogen according to the present invention that is added to the crude oil derived liquid hydrocarbon is renewable, the resultant transportation or heating fuel is considered a fuel having renewable content, or reduced fossil fuel content.

(i) Addition of Renewable Hydrogen

The incorporation of renewable hydrogen into the crude oil derived liquid hydrocarbon according to the present invention encompasses the addition, incorporation or bonding of renewable hydrogen to crude oil derived liquid hydrocarbon. Such reactions include hydrogenation, which includes, without limitation, any reaction in which renewable hydrogen is added to a crude oil derived liquid hydrocarbon through a chemical bond or linkage to a carbon atom. The renewable hydrogen may become bonded to a carbon backbone, a side chain, or a combination thereof, of a linear or ring compound of a crude oil derived liquid hydrocarbon. Hydrogenation reactions may be carried out in the presence of a catalyst.

The addition or incorporation of renewable hydrogen into the crude oil derived liquid hydrocarbon can be achieved by the addition of such hydrogen to an unsaturated or a saturated hydrocarbon. This includes addition of renewable hydrogen to unsaturated groups, such as alkenes or aromatic groups, on the crude oil derived liquid hydrocarbon. Furthermore, the addition or incorporation of hydrogen may be accompanied by the cleavage of a hydrocarbon molecule. This may include a reaction that involves the addition of a hydrogen atom to each of the molecular fragments that result from the cleavage. Without being limiting, such reactions may include ring opening reactions and/or dealkylation reactions. Other reactions that may involve the addition of hydrogen include reactions carried out prior to isomerization and cyclization.

The hydrogenation reactions may be conducted in a "hydrogenation reactor". As used herein, the term "hydrogenation reactor" includes any reactor in which hydrogen is added to a crude oil derived liquid hydrocarbon. The hydrogenation reactor may be a hydrocracking reactor or a "hydrocracker" or any other reactor in which hydrogen becomes bonded to a crude oil derived liquid hydrocarbon, as described hereinafter.

Without being limiting, hydrogenation reactions may involve saturation of aromatics, olefins (alkenes), or a combination thereof. Non-limiting examples of hydrogenation reactions are provided below. Such reactions are known to those of skill in the art and are reproduced from Robinson et al., Practical Advances in Petroleum Processing, Vol. 1, Ed. by Chang S. Hsu and Paul R. Robinson, Springer, New York, Chapter 7, "Hydrotreating and Hydrocraking: Fundamentals" (2006) 177-218.

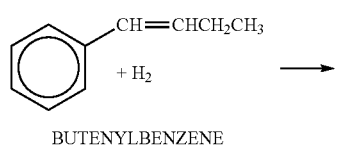

BUTENYLBENZENE

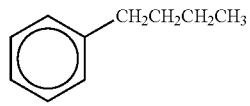

N-BUTYLBENZENE

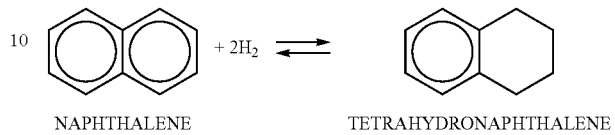

NAPHTHALENE      TETRAHYDRONAPHTHALENE

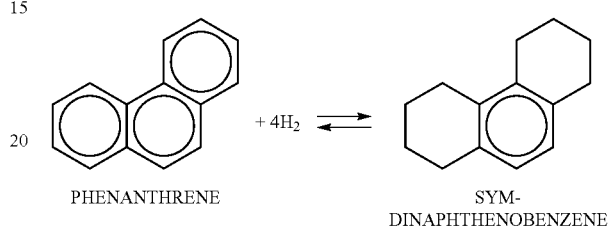

PHENANTHRENE      SYM-DINAPHTHENOBENZENE

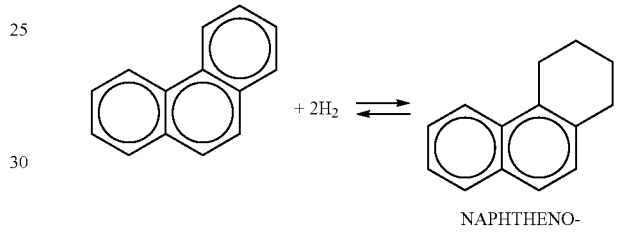

NAPHTHENO-NAPHTHALENE

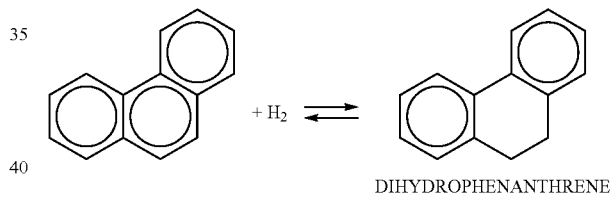

DIHYDROPHENANTHRENE

The following reactions, which are not meant to be limiting in any manner, exemplify how reactions that cleave hydrocarbons incorporate hydrogen atoms into a hydrocarbon molecule. The first reaction is a ring opening reaction and the second is a ring dealkylation.

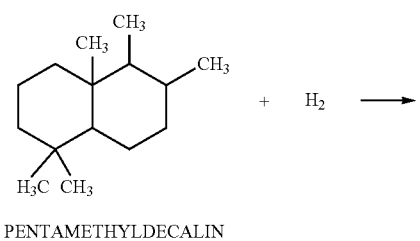

PENTAMETHYLDECALIN

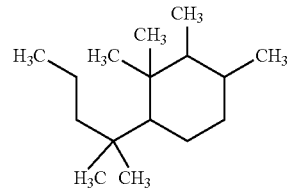

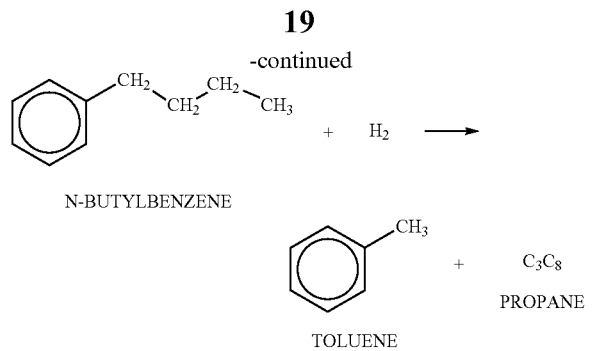

N-BUTYLBENZENE

TOLUENE + $C_3C_8$ PROPANE (ii) Desulfurization of Liquid Hydrocarbon

In the present invention, the renewable hydrogen produced from the combustible fluid feedstock can be combined with a crude oil derived liquid hydrocarbon that is desulfurized. By the term "desulfurized, crude oil derived liquid hydrocarbon", it is meant that a large part or all of the sulfur is removed from a crude oil derived liquid hydrocarbon. In one example of the invention, at least 75%, or at least 85 or 90% of the sulfur is removed from the crude oil derived liquid hydrocarbon.

The sulfur may be removed in a reactor that desulfurizes a crude oil derived liquid hydrocarbon, such as a hydrotreater. The hydrotreater can also remove nitrogen and oxygen.

The desulfurized, crude oil derived liquid hydrocarbon may then be fed to a reactor that operates under conditions to hydrogenate the crude oil derived liquid hydrocarbon with the renewable hydrogen. The reactor can be a hydrocracker, as described below. Sulfur and nitrogen compounds and/or metals are removed before entering the hydrocracking reactor as these components can act as poisons to the hydrocracking catalyst.

(iii) Hydrocracking

As set out above, hydrogenation reactions can be carried out in a hydrocracker. Hydrocracking typically employs a catalyst and hydrogen. Hydrocracking reactions involve the conversion of relatively high-boiling, high molecular weight hydrocarbons into lower-boiling, lower molecular weight hydrocarbons by the breaking of carbon-to-carbon bonds. The breaking of carbon-to-carbon bonds also referred to herein as "cracking" or "hydrocracking", may be carried out in a hydrogenation reactor. In this invention, the cracking in the presence of renewable hydrogen can be carried out in a hydrocracker.

In one embodiment of the present invention, it is preferred that the reactor, to which the renewable hydrogen is introduced, does not cause any significant conversion of organic sulfur into hydrogen sulfide, as would occur in a desulfurization reactor, such as a hydrotreater. In reactors that are operated so as to remove sulfur in such a manner, such as a hydrotreater, a significant part of the renewable hydrogen introduced to the reactor leaves the reactor as $H_2S$, rather than being incorporated into the crude oil derived liquid hydrocarbon by hydrogenation. Thus, according to some embodiments of the invention, the renewable hydrogen is not added to a desulfurization reactor or hydrotreater that primarily or principally carries out desulfurization so as to remove sulfur in the form of $H_2S$.

Hydrocracking converts crude oil derived hydrocarbon to products having lower molecular weight than that of the feed. This results in the products having a lower boiling point relative to the feed. According to a further embodiment of the invention, the "conversion level" in the reactor, such as a hydrogenating or hydrocracking reactor, is between 20 and 100 wt %. By the term "conversion level", it is meant the difference in amount of unconverted crude oil derived liquid hydrocarbon between feed and product divided by the amount of unconverted crude oil derived liquid hydrocarbon in the feed. Unconverted crude oil derived liquid hydrocarbon is material that boils above a specified temperature. Without being limiting, for vacuum gas oil, a typical specified temperature is 650° F. (343° C.). In typical hydrotreating units, which are conducted to remove sulfur, nitrogen and other impurities from the crude oil derived hydrocarbon, the conversion may be less than 20 wt %, more typically less than 15 wt %.

Typically, two catalytic sites catalyze respective cracking and hydrogenation reactions in the hydrocracker. An acid function may catalyze the cracking, while a metal function may catalyze hydrogenation. In certain embodiments, the acidic support consists of amorphous oxides or a mixture of crystalline zeolite and amorphous oxides. The metals providing the hydrogenation function can be noble metals, non-noble metal sulfides from group VIA and group VIIIA. According to some embodiments, the hydrocracker uses a catalyst that is active only for cracking and hydrogenating.

The invention is not limited by the particular feedstock fed to the hydrocracker, although the feed may be gas oil. In some embodiments of the invention, feedstock fed to the hydrocracking operation is one that is difficult to process by either catalytic cracking or reforming. In further embodiments of the invention, such feedstock is characterized by a high polycyclic aromatic content.

Without being limiting, the hydrocracker may receive aromatic cycle oils and coker distillates as feedstock. These feeds may originate from atmospheric and/or vacuum distillation units, delayed cokers, fluid cokers, visbreakers or fluid catalytic cracking units. Middle distillates from a hydrocracker usually meet or exceed finished product specifications, but the heavy naphtha from a hydrocracker may be sent to a catalytic reformer for octane improvement.

The hydrocracking process configuration may include one or multiple stages. According to some embodiments, a single stage hydrocracker is utilized. For single stage hydrocrackers, the oil fed to the hydrocracker may be previously desulfurized as described above. Two stage hydrocracking operations may employ separate respective reactors for desulfurization and cracking According to this embodiment, the renewable hydrogen may be introduced to the reactor in which the cracking reaction is conducted, after desulfurization. In any of the foregoing process configurations, uncracked residual hydrocarbon from the bottom of the reactor may or may not be recycled back to a reactor. Circulation of hydrogen with the feedstock may be utilized in order to reduce catalyst fouling.

(iv) Combined or Simultaneous Desulfurization and Hydrogenation

In one embodiment, a liquid transportation or heating fuel is produced by a process that comprises combining renewable hydrogen with a crude oil derived liquid hydrocarbon and an additional effective amount of hydrogen of sufficient quantity to desulfurize the crude oil derived liquid hydrocarbon. The additional effective amount of hydrogen may be derived from fossil fuel sources. The amount of hydrogen used to desulfurize the crude oil derived liquid hydrocarbon may be determined by those of ordinary skill in the art using known techniques.

The foregoing process is carried out in a reactor under conditions to simultaneously desulfurize and hydrogenate the crude oil derived liquid hydrocarbon. The desulfurization and hydrogenation may be conducted in a reactor that carries out both respective functions. According to some embodiments, as would be appreciated by those of skill in the art, the reactor may use an amorphous catalyst that carries out both hydrotreating and hydrocracking The desulfurization catalyst, or hydrotreating catalyst, is designed to convert organic sulfur in crude oil derived hydrocarbons to $H_2S$, while the hydrogenation catalyst, or hydrocracking catalyst, provides for cracking and hydrogenation of the hydrocarbons. Additionally, the hydrotreating may convert organic nitrogen to ammonia. The conditions used in the reactor are conventional and can be readily selected by those of ordinary skill in the art.

According to some embodiments of the invention, the hydrogen that becomes bonded to the crude oil derived liquid hydrocarbon is greater than or equal to two thirds of the renewable hydrogen that is either contracted for or otherwise introduced to the fuel production facility or reactor. According to further embodiments of the invention, the hydrogen that becomes bonded to the crude oil derived liquid hydrocarbon is greater than or equal to ¾ or ⅞ of the renewable hydrogen that is either contracted for or otherwise introduced to the fuel production facility or reactor.

Additional Refining Steps

Other process steps besides those described above can be carried out in the fuel production facility to produce the transportation or heating fuel. Examples of such process steps include isomerization and catalytic reforming. Prior to isomerization, the crude oil derived hydrocarbon may be sent to a hydrogenation reactor, which may saturate olefins to paraffins and saturate benzene. Both isomerization and catalytic reforming increase the octane rating of the liquid hydrocarbon, which is a measure of the likelihood that a gasoline or liquid petroleum fuel will self-ignite during compression. The higher the number, the less prone the engine is to uncontrolled ignition, including pre-ignition. Those of ordinary skill herein understand that different technology configurations may be used and the embodiments and examples discussed herein are non-limiting, and accordingly that other known or later-developed technologies for processing and producing fuels, including various different configurations, may be utilized in conformity with the present invention.

Fuel Product

As mentioned previously, if portions of the hydrogen contained in fuel produced from a fuel production facility are derived from renewable hydrogen as set forth above, the fuel product produced by the fuel production facility may be considered a renewable fuel or a fuel having renewable content.

The fuel produced in accordance with the invention may be referred to as a petroleum-based fuel. Fuel produced by a fuel production facility is typically liquid at ambient temperature and pressure and includes transportation fuel for use in motor vehicles, motor vehicle engines, non-road vehicles or non-road engines, or jet fuel and heating oil.

Liquid transportation or heating fuel products or portions thereof resulting from the present invention may be considered renewable fuel, and qualify for renewable fuel credits as described herein. In addition, the process itself may generate low carbon fuel credits. In some embodiments of this invention, the combustible fluid feedstock used to make renewable hydrogen is derived or purified directly from crude biogas. In such embodiments the renewable hydrogen derived from such combustible fluid feedstock is incorporated into the liquid transportation or heating fuel product to make a renewable or partially renewable fuel. In some of these embodiments, the apparatus used to transport the combustible fluid feedstock is a shipping container or pipeline that does not carry natural gas.

However, in additional embodiments of the invention where a natural gas pipeline or other like commercial distribution system is utilized as the apparatus to transport combustible fluid feedstock to the fuel production facility, then the combustible fluid feedstock, upon withdrawal from the apparatus for use at the fuel production facility, may comprise methane derived from biogas, methane derived from natural gas or mixtures of methane derived from both natural gas and biogas. In such embodiments, this withdrawn combustible fluid feedstock can be used to produce renewable hydrogen and make a liquid transportation or heating fuel that has renewable content or is otherwise considered a renewable or partially renewable fuel.

Government authorities have recognized that it does not make any difference, in terms of the beneficial environmental attributes associated with the use of biogas, whether the displacement of fossil fuel occurs in a fungible natural gas pipeline, or in a specific fuel production facility that draws combustible fluid feedstock from that pipeline. In fact, similar considerations are widely accepted with respect to electricity generated by renewable biomass that is placed into a commercial electricity grid. A party buying the renewable power is credited with doing so in state renewable portfolio programs even though the power from these sources is placed in the fungible grid and the electrons produced by a renewable source may never actually be used by the party purchasing it. In essence these programs assume that the renewable power purchased and introduced into the grid is in fact used by the purchaser, even though all parties acknowledge that use of the actual renewable-derived electrons cannot be verified once placed in the fungible grid. Governments have also recognized that that this approach will ultimately further the GHG reduction and energy security goals set out in various pieces of legislation including the EISA and the RFS, including RFS2.

As a result, under certain current regulations, producers may treat the combustible fluid feedstock withdrawn from a pipeline as renewably derived, effectively taking into account the displacement of fossil derived natural gas in the pipeline by renewably derived combustible fluid feedstock, provided that they demonstrate that a verifiable contractual pathway exists and that such pathway ensures that (1) a specific volume of combustible fluid feedstock derived directly from biogas was placed into a commercial pipeline that ultimately serves the fuel production facility; (2) that the volume of combustible fluid feedstock withdrawn into this facility from that pipeline matches the volume of combustible fluid feedstock derived directly from biogas placed into the pipeline system; and (3) that the quantity of combustible fluid feedstock for which renewable fuel credits were generated was sold for use as transportation or heating fuel and for no other purpose. Where such conditions are satisfied, liquid transportation or heating fuel made using combustible fluid feedstock withdrawn from a natural gas pipeline may qualify for renewable fuel credits. It should be understood that the requirements for the combustible fluid feedstock to qualify as renewable or renewably derived may change according to government standards and that the invention is not limited to the current rules as would be known by those of skill in the art.

In accordance with the invention, a first amount of combustible fluid feedstock is introduced to apparatus for delivering combustible fluid feedstock to a fuel production facility and a second amount is withdrawn for use at the fuel production facility. The first amount of combustible fluid feedstock may also be referred to as the introduced amount and the second amount of combustible fluid feedstock that is withdrawn from the apparatus may also be referred to as the withdrawn amount. According to one delivery mode of the invention where a natural gas pipeline is used or other like commercial distribution system, the withdrawn amount of combustible fluid feedstock is "approximately equal" to the first amount of combustible fluid feedstock. By "approximately equal", it is meant that the energy content or heat value of the second amount of combustible fluid feedstock does not substantially vary from the energy or heat value of the introduced amount of combustible fluid feedstock, such as by more than about 10%, more preferably by more than about 5%. The energy content or heat value may be measured using British thermal units (BTU) or joules for a given volume of the combustible fluid feedstock.

It will be understood that the introduced amounts and the withdrawn amounts of combustible fluid feedstock may not be all the combustible fluid feedstock that is introduced into or withdrawn from the apparatus for delivering combustible fluid feedstock. For example, a biogas production facility may introduce more combustible fluid feedstock into a pipeline than will ultimately be processed in accordance with the invention, and similarly, a fuel production facility may withdraw more combustible fluid feedstock from a pipeline than will ultimately be used in accordance with the invention. It will also be understood that quantities of combustible fluid feedstock may be introduced into and withdrawn from the apparatus for delivering combustible fluid feedstock in batch sizes or at rates that are not identical at the introduction and withdrawal points.

Combustible fluid feedstock that has been delivered to an apparatus for delivering combustible fluid feedstock to a fuel production facility, and is withdrawn for use, may comprise methane derived from natural gas or mixtures of natural gas and biogas.

According to some embodiments of the invention, one or more parties can cause a fuel production facility to use combustible fluid feedstock in a process for producing renewable hydrogen (further described herein) to make transportation or heating fuel. In other embodiments of the invention, one or more parties can cause combustible fluid feedstock, derived from crude biogas, to be introduced to an apparatus for delivering combustible fluid feedstock to a fuel production facility, and withdrawal of combustible fluid feedstock for use in producing renewable hydrogen to make transportation or heating fuel.

The term "cause", as used herein means to arrange or bring about, either directly or indirectly, including through commercial arrangements such as a written agreement, verbal agreement or contract.

In some embodiments of the invention, a party causes a fuel production facility to (a) withdraw combustible fluid feedstock from an apparatus for delivering combustible fluid feedstock; and (b) process the combustible fluid feedstock to produce renewable hydrogen for use in making transportation or heating fuel, preferably transportation or heating fuel with renewable content. In such embodiments the party is typically a biogas producer or one or more third parties that supply or deliver the combustible fluid feedstock to the fuel production facility or both. The biogas producer, including an importer or intermediate party, that supplies or delivers the combustible fluid feedstock to the fuel production facility, preferably enters into a contract or agreement with a fuel production facility to sell combustible fluid feedstock derived from crude biogas, or to introduce combustible fluid feedstock derived from biogas into an apparatus for delivering same, for use in a process for producing transportation or heating fuel. Such contract may meet the standards of Government authorities for the generation of renewable fuel credits. Combustible fluid feedstock is then used or processed to make renewable hydrogen which is then used to make transportation or heating fuel. In some embodiments of the invention, renewable hydrogen is combined with a desulfurized, crude oil derived liquid hydrocarbon in a reactor under conditions to hydrogenate the liquid hydrocarbon with the renewable hydrogen. In other embodiments of the invention, the renewable hydrogen is combined with a crude oil derived liquid hydrocarbon and an additional effective amount of hydrogen of sufficient quantity to desulfurize the crude oil derived liquid hydrocarbon in a reactor in which desulfurization and hydrogenation of the crude oil derived liquid hydrocarbon occurs in the same reactor, and preferably simultaneously.

According to further embodiments of the invention, a party causes combustible fluid feedstock that has been derived from crude biogas to be introduced to an apparatus for delivering combustible fluid feedstock to a fuel production facility. In such embodiment, the party may be a fuel production facility or an intermediate party. The fuel production facility or the intermediate party preferably enters into a contract or agreement with a biogas producer or supplier to purchase combustible fluid feedstock derived from crude biogas for use in a process for producing transportation or heating fuel. Such contract may meet the standards of Government authorities for the generation of renewable fuel credits. Combustible fluid feedstock is then used or processed to make renewable hydrogen which is then used to make transportation or heating fuel. In some embodiments of the invention, renewable hydrogen is combined with a desulfurized, crude oil derived liquid hydrocarbon in a reactor under conditions to hydrogenate the liquid hydrocarbon with the renewable hydrogen. In other embodiments of the invention, the renewable hydrogen is combined with a crude oil derived liquid hydrocarbon and an additional effective amount of hydrogen of sufficient quantity to desulfurize the crude oil derived liquid hydrocarbon in a reactor in which desulfurization and hydrogenation of the crude oil derived liquid hydrocarbon occurs in the same reactor, and preferably simultaneously.

The foregoing commercial arrangement or agreements may include one or more conditions, including the following conditions: (i) the fuel production facility or other party arranges to procure an amount or amounts of combustible fluid feedstock, such as a volume amount or a heat or energy content; (ii) the combustible fluid feedstock is only to be procured by the party specified in the commercial arrangement or agreement; (iii) the amount of combustible fluid feedstock, such as a volume amount or a heat or energy content, that is withdrawn from an apparatus for delivering a combustible fluid feedstock, such as a commercial distribution system, is withdrawn in a manner and at a time consistent with the transport of the combustible fluid feedstock between injection and withdrawal points; (iv) the amount of combustible fluid feedstock introduced and withdrawn from an apparatus for delivering a combustible fluid feedstock is measured, such as by metering; (v) an apparatus for delivering a combustible fluid feedstock serves the fuel production facility; (vi) the specified quantity of combustible fluid feedstock introduced and the quantity withdrawn is only used for transportation or heating purposes; and any combination of conditions (i)-(vi).

Meeting Renewable and Low Carbon Fuel Targets

The invention advantageously provides a methodology for meeting renewable fuel targets or mandates established by governments, including legislation and regulations for transportation or heating fuel sold or introduced into commerce in the United States. Examples of such legislation include the EISA and California AB 32—The Global Warming Solutions Act, which respectively established an RFS and a Low Carbon Fuel Standard (LCFS).

The present invention may allow for the generation of a "credit" or "renewable fuel credit", which means any rights, credits, revenues, offsets, greenhouse gas rights, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority or a private contract. According to an embodiment of the invention, the renewable fuel credit is a certificate, record, serial number or guarantee, in any form, including electronic, which evidences production of a quantity of fuel meeting certain lifecycle GHG emission reductions relative to a baseline set by a government authority. Preferably, the baseline is a gasoline baseline. Non-limiting examples of credits include RINs and LCFS credits.

The foregoing process for producing a transportation or heating fuel may qualify for the generation of RINs under the EISA legislation, and LCFS credits under AB 32 as a result of the renewable nature and favorable GHG profile of the input biogas. A RIN is a certificate which acts as a tradable currency for managing compliance under the RFS, and an LCFS credit is a certificate which acts as a tradable currency for managing compliance under California's LCFS. A RIN has numerical information associated with the production of a qualifying renewable fuel in accordance with regulations administered by the EPA for the purpose of managing the production, distribution and use of renewable fuels for transportation or other purposes. As described previously, the utilization of renewable feedstocks to produce transportation or heating fuel has been promoted by various governments, including the United States government through the EISA legislation. One of the goals of the act is to increase the production and use of clean renewable fuels. In order to achieve this objective, EISA mandates the use of aggregate volumes of different categories of renewable biofuels within the total pool of transportation or heating fuels sold or introduced into commerce in the United States.

The mandated annual targets of renewable content in transportation or heating fuel are implemented through an RFS program that uses RINs to track and manage the production, distribution and use of renewable fuels for transportation or heating purposes. Prorated mandated volume requirements are determined for each "obligated party", such as individual gasoline and diesel producers and/or importers, based on their annual production and/or imports. Each year, obligated parties are required to meet their prorated share of the RFS mandates by accumulating trading certificates, such as RINs, either through blending designated quantities of different categories of biofuels, or by purchasing from others the RINs of the required biofuel categories. In the U.S., the EPA is responsible for developing regulations for RINs, as required by section 211(o) of the Clean Air Act, as amended by EISA.

The EPA issued regulations in 2007 referred to as "RFS1". In a subsequent rulemaking on March 2010, EPA made a number of changes to the program, known as "RFS2". The process disclosed above may advantageously produce a renewable transportation or heating fuel that would be eligible for RINs, such as under RFS2.

Renewable fuel producers may generate RINs for fuels from feedstocks meeting the definition of renewable biomass. A fuel is considered a renewable fuel if it meets the following requirements: (i) It is a fuel that is produced from renewable biomass. (ii) The fuel is used to replace or reduce the quantity of fossil fuel present in a transportation fuel, heating oil or jet fuel. (iii) The fuel has lifecycle GHG emissions that are at least 20 percent less than baseline lifecycle GHG emissions. (See 40 C.F.R. §80.1401(1)).

The process of the present invention is believed to meet each of the foregoing legislative requirements. Biogas is sourced from waste organic matter, including landfill biogas that is formed from the biogenic portion of landfill material. Thus, the transportation or heating fuel is considered to be produced from a renewable biomass. Moreover, as described above, the renewable hydrogen is combined with a crude oil derived liquid hydrocarbon so that it becomes incorporated into a liquid transportation or heating fuel that is the product of the fuel production facility. Accordingly, the fuel is used to replace or reduce the quantity of fossil fuel present in a transportation or heating fuel. With respect to the requirement that the fuel has lifecycle GHG emissions that are at least 20 percent less than baseline lifecycle GHG emissions, it may be found that biogas, including that derived from landfills, meets this threshold.

Accordingly, the transportation or heating fuel produced by the process of the present invention or intermediates produced thereunder may be eligible for generation of RINs. According to some embodiments of the invention, the RINs can be generated by the producer of the biogas and transferred to a purchaser of the combustible fluid feedstock who makes renewable hydrogen and subsequently a transportation or heating fuel comprising renewable hydrogen. According to other embodiments of the invention, RINs can be generated by a producer of the renewable hydrogen or the transportation or heating fuel comprising the renewable hydrogen. Advantageously, acquisition of RINs by purchase or generation allows an obligated party to certify compliance with mandated renewable fuel volumes, hold the RIN for future compliance or trade it, as set out below.

Furthermore, the process of the present invention is believed to meet the requirements for qualification to generate advanced biofuel RINs. An advanced biofuel is a category of renewable fuel. A fuel is considered an advanced biofuel if it is a renewable fuel other than ethanol from corn starch, and if it has lifecycle GHG emissions that are less than 50% less than the baseline lifecycle GHG emissions or lifecycle GHG emissions for gasoline. Under the current regulations, the fuel production pathway for biogas has been pre-qualified as meeting the requirements of advanced biofuel (see 40 C.F.R. Table 1 to §80.1426). In addition, it may be found that the lifecycle GHG emissions meet the 50% reduction threshold.

It should be understood that the regulations under EISA, including RIN requirements and the criteria for categorization of a fuel under a particular fuel category, such as life cycle GHG emission thresholds, are described herein in accordance with current regulations and that the invention is not limited to current rules and will provide benefits in relation to subsequent rule changes thereof.

Renewable Identification Numbers (RINs)

The present invention also provides a method comprising generating numerical information to support a renewable fuel credit associated with a product produced in accordance with the method of the invention, which product is selected from (i) the combustible fluid feedstock derived from biogas; (ii) the renewable hydrogen; (iii) the transportation or heating fuel comprising renewable hydrogen; and (iv) the crude biogas.

A RIN contains digital or numerical information about a renewable fuel. A RIN is assigned to a batch of fuel for the purpose of tracking its production and use, and provides for the use of trading activities to meet environmental obligations as provided by the United States EPA's RFS implemented according to EISA. A RIN is generated upon production or importation of a renewable fuel. RINs are transferred with the renewable fuel through the distribution system until they are separated from the fuel by parties who are entitled to make such separation (generally refiners, importers, or parties that blend renewable fuels into finished fuels). Separation of a RIN from a volume of renewable fuel means termination of the assignment of the RIN to a volume of renewable fuel, as set out below. According to current regulations, RINs contain parameters or codes that represent numerical information about the fuel or product. The numerical information that is generated may relate to the combustible fuel feedstock, crude biogas or to the transportation or heating fuel or fuel intermediate produced by the process of the invention. According to the present invention, a party may generate RINs comprising numerical information relating to an amount of fuel or fuel product representing at least three parameters selected from (i) the type of renewable fuel that the product is; (ii) the year in which the fuel was produced or the year the numerical information was produced; (iii) registration number associated with the producer or importer of the renewable fuel or product; and (iv) serial number associated with a batch of the renewable fuel or product. Such numerical information relates or is associated with a product, or fuel product, selected from (a) combustible fluid feedstock derived from crude biogas, (b) crude biogas, (c) renewable hydrogen, (c) transportation or heating fuel comprising renewable hydrogen, or (d) transportation or heating fuel intermediates comprising renewable hydrogen.

The numerical information may also include one or more of the following parameters selected from: (i') a number identifying that the numerical information is assigned to a volume of fuel or separated; (ii') a registration number associated with the facility at which the fuel was produced or imported; (iii') a number representing a value related to an equivalence value of the fuel; (iv') a number representing a first-volume numerical information associated with a batch of renewable fuel; and (v') a number representing a last-volume numerical information associated with a batch of renewable fuel.

According to further embodiments of the invention, the numerical information may include codes representing information about the fuel. Such codes may include a K-code, Y-code, C-code, F-code, B-code, R-code, D-code, S-code and an E-code, wherein, under current regulations:

K is a code identifying that the RIN is assigned to a volume of fuel or separated.
K has a value of 2 when the RIN has been separated from a volume of renewable fuel.
Y-code or YYYY: year in which the fuel was produced.
C-code or CCCC: registration number associated with the producer or importer of the renewable fuel.
F-code or FFFFF: a registration number associated with the facility at which the fuel was produced or imported.
B-code or BBBBB: serial number associated with a batch of the renewable fuel.
R-code or RR: a two digit number representing the relative energy density of the renewable fuel, where, under current regulations, this is the equivalence value, which is the ratio of the energy density of the renewable fuel to the energy density of ethanol multiplied by 10.
D-code or D: a number identifying the type of renewable fuel.
S-code or SSSSSSSS: a number representing the first volume-RN associated with a batch of renewable fuel.
E-code or EEEEEEEE: a number representing the last volume-RN associated with a batch of renewable fuel.

The numerical information contained in the RIN may contain at least 3, 4, 5, 6, 7, 8 or 9 of the above-mentioned numerical codes. The codes may contain a predetermined number of characters as required by prevailing regulations. Under current regulations, a RIN contains much of the foregoing information and other information in the form of data elements that are introduced into a web-based system administered by the EPA known as the EPA Moderated Transaction System, or "EMTS". Up to Jul. 1, 2010, the numerical information had the format of a 38 character numeric code of the format KYYYYCCCCFFFFF-BBBBBRRDSSSSSSSSEEEEEEEE. It should be appreciated that the numerical information contained in the RIN may vary depending upon prevailing regulations. That is, as would be understood by those of skill in the art, the information required to generate a RIN may be updated over time by regulatory bodies.

The numerical information described herein or portion thereof is provided to a government regulatory agency, including the EPA, in connection with generating a RIN. In some embodiments of the invention, the numerical information is also provided to a fuel production facility or to a purchaser of biogas derived combustible fluid feedstock. The numerical information described herein or portions thereof may be stored electronically in computer readable format.

Generation of RINs

A RIN may be generated by parties including renewable fuel producers, importers, biogas producers, generators of renewable hydrogen and fuel production facilities. According to current regulations, RINs may be generated if the fuel is designated or intended for use as transportation fuel, heating fuel or jet fuel. (See 40 C.F.R. §80.1426(c)(1)). The process for the generation and assignment of RINs by producers and importers is set out in 40 C.F.R. §80.1426, which states in part that producers and importers of renewable fuel must generate RINs to represent that (i) the fuel qualifies for a D-code, or EPA has approved a petition for use of a D-code, and (ii) demonstrate that the fuel is produced from renewable biomass.

As used herein, a producer or importer that generates RINs may include a producer or importer of combustible fluid feedstock, which is intended for use in a fuel production facility to make a transportation or heating fuel. In some embodiments of the invention, the producer or importer of biogas derived combustible fluid feedstock generates a RIN. According to further embodiments of the invention, the producer or importer that generates RINs may include a fuel production facility that produces partially renewable fuel using renewable hydrogen. Generally, producers or importers can include a biogas production facility, a fuel production facility or an intermediary party that facilitates the transfer of combustible fluid feedstock.

When used as renewable fuel, biogas made from landfills, sewage and waste treatment plants and manure digesters under the RFS qualifies for a D code of 5, which classifies it as an "advanced biofuel". The combustible fluid feedstock of the present invention is produced or sourced from renewable biomass, including biogas generated from non-separated landfill waste. Accordingly, the combustible fluid feedstock is eligible to generate RINs. (see 40 CFR Table 1 to §80.1426).

In order to generate a RIN associated with renewable fuel, a producer or importer registers with an administrator of the EPA (referred to herein as an "EPA administrator"), according to prevailing regulations. (See 40 C.F.R. §80.1450(b)). Registration with the EPA administrator is in advance of the renewable fuel production date. Information required in the registration form may include, but is not limited to, the name, business address, contact name and telephone number of the producer or importer and location of records. (See 40 C.F.R.

§80.76). The EPA will supply a registration number to the producer or importer and this number will be used in reports by the EPA administrator. The EPA will also assign the permitted categories of fuels that can be produced under the registration, and the D-code that is assigned to each type of permitted fuel for RIN generation. The producer or importer will also receive company and facility identification numbers, issued by the EPA, typically prior to the generation of any RINs for their fuel. (See 40 C.F.R. §80.1450). In the present invention, the biogas production facility, an intermediary or the fuel production facility could register or provide information with the EPA to generate a RIN.

The fuel type code (D-code) of the RIN is an important designation, as the RFS mandate volumes are set by four nested category groups with different types of fuels qualifying for each category. The nested category groups are differentiated by net GHG savings relative to baseline and by the fuel type and feedstock source as follows:

a) total renewable biofuel—greater than 20% GHG savings unless grandfathered, comprised of conventional biofuels (D code 6) and advanced biofuels (D code 3, 4, 5, or 7)
b) total advanced biofuel—greater than 50% GHG savings, comprised of cellulosic biofuels (D code 3 or 7), biomass-based diesel (D-code 4 or 7), and other advanced biofuels (D-code 5)
c) cellulosic biofuels—greater than 60% GHG savings, comprised of biofuel derived from lingo-cellulosic material (D code 3) and bio-diesel derived lingo-cellulosic material (D-code 7)
d) biomass-based diesel—greater than 50% GHG savings, comprised of conventional biodiesel (D-code 4) or cellulosic diesel (D-code 7)

The D-code is assigned based upon the fuel type, the feedstock, and the production process. Each specific combination of the three components, or fuel pathway, is assigned a RIN D-code, which is used in designating the renewable fuel category (renewable fuel, biomass-based diesel, advanced biofuel, cellulosic biofuel) for which it qualifies.

Certain pathways have D-codes predetermined by the regulations, while other new pathways must undergo a petition for evaluation by the EPA. When used in transportation, biogas made from landfills, sewage and waste treatment plants and manure digesters under the RFS has a pre-determined D code of 5, which classifies it as an "advanced biofuel" (see 40 CFR Table 1 to §80.1426). The biogas combustible fluid feedstock of the present invention would qualify to generate a RIN with a D code of 5. Alternatively, a petition could be made to the EPA to allow the fuel produced by the present invention or any intermediate produced thereunder to be assigned a D-code.

The producer or importer that generates a RIN reports information pertaining to the renewable fuel, including, but not limited to, an amount of each batch produced, where "batch" means a discrete quantity of renewable fuel produced or imported and assigned a unique batch-RIN. (See 40 C.F.R. §80.1451(b)(ii)(J)). This information may be submitted to the EPA using the EPA's Moderated Transaction System ("EMTS").

Depending on the prevailing regulations, the producer or importer may report or provide to a government regulatory agency part or all the following information under 40 C.F.R. §80.1451 for each batch of renewable fuel produced or imported, including, but not limited to, the RIN generator's name; the RIN generator's EPA company registration number; the renewable fuel producer or importer's EPA facility registration number; the applicable reporting period; the quantity of RINs generated for each batch according to 40 C.F.R. §80.1426; the production date of each batch; the fuel type of each batch; the volume of each batch produced; the types and quantities of feedstock used; the process(es) and feedstock(s) used and proportion of renewable volume attributable to each process and feedstock; and a list of the RINs generated and an affirmation that the feedstock(s) used for each batch meets the definition of renewable biomass as defined in 40 C.F.R. §80.1401. Furthermore, producers or importers of biogas used as transportation fuel, heating fuel or jet fuel as described in 40 C.F.R. §80.1426(f)(10) and (11), shall report all of the following: the total energy produced and supplied for use as a fuel, in units of energy (for example, MMBtu or MW) based on metering of gas volume or electricity; and the name and location of where the fuel is sold for such uses.

Transferring RINs

The numerical information or RINs associated with the combustible fluid feedstock or renewable fuel may be provided to a government regulatory agency and a purchaser of the combustible fluid feedstock or renewable fuel for transfer to an obligated party.

Advantageously, as set out above, transfer of the RIN to an obligated party or the generation of a RIN by an obligated party may allow an obligated party to certify compliance with mandated renewable fuel volumes, or to subsequently separate the RINs and then sell or trade them. An obligated party may include, but is not limited to, any fuel production facility, including a refiner that produces gasoline or diesel fuel within the 48 contiguous states or Hawaii, or any importer that imports gasoline or diesel fuel into the 48 contiguous states or Hawaii. (See 40 C.F.R. §80.1406).

An obligated party registers with the EPA. (See 40 C.F.R. §80.1450(a)). The information specified for registration is set out in 40 C.F.R. §80.76. An obligated party receives an EPA-issued identification number prior to engaging in any transaction involving RINs in accordance with 40 C.F.R. §80.1450(a).

When a party transfers ownership of a fuel and its associated RIN, the transferor provides to the transferee, product transfer documents. (See 40 C.F.R. §80.1453). Such documents identify the renewable fuel and any RINs (whether assigned or separated) and may include part of all of the following information, as applicable: the name and address of the transferor and transferee; the transferor's and transferee's EPA company registration numbers; the volume of renewable fuel that is being transferred; the date of the transfer; the per volume price of the RIN, if applicable; the quantity of RINs being traded; the renewable fuel type (D-code); the assignment code (K-code); the RIN generation year; the associated reason for the transaction; and any other applicable requirements.

Other information submitted to the EPA in connection with the transfer of RINs may be in the form of RIN transaction reports, listing RIN transactions, and records relating to the use of RINs for compliance including RIN activities. (See 40 C.F.R. §80.1454).

Separating RINs

As set out above, separation of a RIN from a volume of renewable fuel means termination of the assignment of the RIN to a volume of renewable fuel. RIN separation is typically carried out by a fuel blender, importer or obligated party.

Separating RINs means that RINs are not subject to requirements to transfer them with the renewable fuel to which they are associated. That is, a separated RIN can be transferred to another party without simultaneously transferring a volume of renewable fuel to that same party. Without limitation, this allows a party to conduct RINs transactions, such as trading or selling the RIN, independent of the fuel. According to prevailing regulations, when a RIN is separated, the K code of the RIN is changed to 2.

Separation of RINs may be conducted in accordance with prevailing rules and regulations, as currently provided in 40 C.F.R. §80.1129 and 40 C.F.R. §80.1429. RINs generated in accordance with the invention may be separated and may also be traded.

In accordance with certain embodiments of the invention, the party separating the RIN may be a fuel production facility, or a party that receives and transports combustible fluid feedstock to a fuel production facility.

Generation and Transfer of LCFS Credits

The invention also can provide a methodology for meeting low carbon fuel standards established by states within the United States or other government authorities. Transportation or heating fuels, including fuels made from crude oil derived liquid hydrocarbons, have a net GHG emission level associated with their production and this level can be compared against a standard, typically the greenhouse emission standard for gasoline set by the EPA. Due to legislative initiative and mandates, demand for renewable transportation or heating fuels with favorable net GHG emission reductions is increasing. For example, the mix of fuel that oil refineries and distributors sell into the California market can be required to meet established targets for GHG emissions. California's LCFS can require increasing reductions in the average lifecycle GHG emission of most transportation fuels. Targets can be met by trading of credits generated from the use of fuels with a lower GHG emission value than a gasoline baseline. Similar legislation has been implemented by the province of British Columbia, Canada, the United Kingdom and by the European Union and is under consideration in certain U.S. states besides California. It should be understood, however, that the invention is not limited to any particular jurisdiction in which a credit can be attained for the fuel produced in accordance with the invention.

The conversion of waste organic material into partially renewable or renewable liquid transportation or heating fuel reduces the utilization of fossil fuels. It also improves the net GHG footprint of the liquid transportation or heating fuel and provides a commercial use for waste organic material. These benefits can support the acquisition of a GHG certificate or credit that may or may not be tradable. The certificate or credit may be associated with the transportation fuel or heating fuel and represents or is proportional to the amount of lifecycle GHG emissions reduced or replaced. Methane derived from biogas has a better GHG lifecycle than that derived from natural gas.

Under RFS and LCFS, fuels are characterized by their lifecycle GHG emissions relative to baseline emissions values. For example, under RFS, advanced biofuels have the requirement that they have lifecycle GHG emissions that are at least 50 percent less than baseline lifecycle GHG emissions. To determine this measure, analyses are conducted to calculate the net GHG impact of the use of particular fuels, and are compared by reference to the use of gasoline per unit of fuel energy. Lifecycle GHG emissions evaluations generally consider GHG emissions of each: (a) the feedstock production and recovery (including if the carbon in the feedstock is of fossil origin (such as with oil or natural gas) or of atmospheric origin (such as with biomass)), direct impacts like chemical inputs, energy inputs, and emissions from the collection and recovery operations, and indirect impacts like the impact of land use changes from incremental feedstock production; (b) feedstock transport (including energy inputs, and emissions from transport); (c) fuel production (including chemical and energy inputs, emissions and byproducts from fuel production (including direct and indirect impacts)); and (d) transport and storage prior to use as a transport fuel (including chemical and energy inputs and emissions from transport and storage).

Advantageously, the use of combustible fluid feedstock to make renewable hydrogen and transportation or heating fuel therefrom reduces the lifecycle GHG emissions compared to the conventional process of using natural gas to make non-renewable hydrogen and fuel therefrom. Accordingly, the fuel pathway of the present invention may be eligible for the generation of LCFS credits as a result of the GHG savings. LCFS credits would be generated in proportion to the net GHG savings generated relative to gasoline. Such credits would have associated numerical information, and could be traded by the credit generator, an intermediary, or party obligated under the LCFS.

In addition, this invention could also permit the generation of either or both RINs and LCFS credits.

The invention claimed is:

1. A method of transforming waste organic material to produce a liquid transportation or heating fuel comprising:
   (a) subjecting waste organic material to anaerobic digestion by microorganisms in a biogas production facility that incorporates apparatus to collect the microbially generated biogas;
   (b) collecting an amount of crude biogas from the biogas production facility;
   (c) removing impurities from the crude biogas to yield a combustible fluid feedstock;
   (d) introducing a first amount of the combustible fluid feedstock from step (b) or (c) to apparatus for delivering a combustible fluid feedstock to fuel production facility;
   (e) generating numerical information relating to the first amount of combustible fluid feedstock or crude biogas comprising information representing at least 3 parameters selected from:
      (i) the type of renewable fuel that it is;
      (ii) year in which the combustible fluid feedstock was produced;
      (iii) a registration number associated with the producer or importer of the combustible fluid feedstock; and
      (iv) a serial number associated with a batch of the combustible fluid feedstock; and
   (f) withdrawing for use at a fuel production facility a second amount of combustible fluid feedstock approximately equal to the first amount of combustible fluid feedstock;
   (g) processing at the fuel production facility the second amount of combustible fluid feedstock to produce renewable hydrogen; and
   (h) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

2. The method of claim 1, wherein the biogas production facility is a landfill, a waste treatment facility or a manure digestion facility.

3. The method of claim 1, wherein the reactor is a hydrogenation reactor.

4. The method of claim 1, wherein the reactor is a hydrocracker.

5. The method of claim 1, wherein the liquid transportation or heating fuel is selected from gasoline, diesel, heating oil and jet fuel.

6. The method of claim 1, wherein a liquid transportation fuel is produced in step (h).

7. A method of producing a transportation or heating fuel comprising:
- (a) causing a first amount of combustible fluid feedstock to be introduced to apparatus for delivering a combustible fluid feedstock to a fuel production facility, said first amount of combustible fluid feedstock being derived from a crude biogas that was generated by anaerobic digestion and from which impurities were removed following collection from a biogas production facility;
- (b) withdrawing for use at a fuel production facility, a second amount of combustible fluid feedstock approximately equal to the first amount of combustible fluid feedstock;
- (c) processing at the fuel production facility the second amount of combustible fluid feedstock to produce renewable hydrogen;
- (d) producing a third amount of liquid transportation or heating fuel by a process that comprises combining renewable hydrogen derived from the second amount of combustible fluid feedstock with a desulfurized, crude oil derived liquid hydrocarbon in a reactor under conditions to hydrogenate the liquid hydrocarbon with the renewable hydrogen; and
- (e) receiving and storing numerical information relating to the first amount of combustible fluid feedstock or crude biogas comprising information representing at least 3 parameters selected from:
  - (i) the type of renewable fuel that it is;
  - (ii) year in which the combustible fluid feedstock was produced;
  - (iii) a registration number associated with the producer or importer of the combustible fluid feedstock; and
  - (iv) serial number associated with a batch of the combustible fluid feedstock.

8. The method of claim 7, wherein the biogas production facility is a landfill, a waste treatment facility or a manure digestion facility.

9. The method of claim 7, wherein the reactor is a hydrogenation reactor.

10. The method of claim 7, wherein the reactor is a hydrocracker.

11. The method of claim 7, wherein the liquid transportation or heating fuel is selected from gasoline, diesel, heating oil and jet fuel.

12. The method of claim 7, wherein a liquid transportation fuel is produced in step (d).

13. A method of producing a combustible fluid feedstock for use in producing a transportation or heating fuel, said method comprising:
- (a) subjecting waste organic material to anaerobic digestion by microorganisms in a biogas production facility that incorporates apparatus to collect the microbially generated biogas;
- (b) collecting an amount of crude biogas from the biogas production facility;
- (c) removing impurities from the crude biogas to yield a combustible fluid feedstock;
- (d) generating numerical information relating to the first amount of combustible fluid feedstock or crude biogas comprising information representing at least 3 parameters selected from:
  - (i) the type of renewable fuel that it is;
  - (ii) year in which the combustible fluid feedstock was produced;
  - (iii) a registration number associated with the producer or importer of the combustible fluid feedstock; and
  - (iv) a serial number associated with a batch of the combustible fluid feedstock; and
- (e) introducing a first amount of combustible fluid feedstock from step (b) or (c) to apparatus for delivering a combustible fluid feedstock to fuel production facility; and
- (f) causing a fuel production facility to use combustible fluid feedstock in a process for producing transportation or heating fuel, said process comprising:
  - (i') withdrawing for use at a fuel production facility a second amount of combustible fluid feedstock from the apparatus approximately equal to the first amount of combustible fluid feedstock;
  - (ii') processing the second amount of combustible fluid feedstock to produce renewable hydrogen; and
  - (iii') combining renewable hydrogen derived from the second amount of combustible fluid feedstock with a desulfurized, crude oil derived liquid hydrocarbon in a reactor under conditions to hydrogenate the liquid hydrocarbon with the renewable hydrogen.

14. The method of claim 13, wherein the biogas production facility is a landfill, a waste treatment facility or a manure digestion facility.

15. The method of claim 13, wherein the reactor is a hydrogenation reactor.

16. The method of claim 13, wherein the reactor is a hydrocracker.

17. The method of claim 13, wherein the transportation or heating fuel is selected from gasoline, diesel, heating oil and jet fuel.

18. The method of claim 13, wherein in step (f) the fuel production facility is a transportation fuel production facility and wherein the combustible fluid feedstock is for use in the production of a transportation fuel.

19. A method of producing a transportation or heating fuel comprising:
- (a) receiving combustible fluid feedstock in accordance with an arrangement with a producer or supplier of combustible fluid feedstock derived from crude biogas, said arrangement relating to the use of combustible fluid feedstock in a process for producing liquid transportation or heating fuel;
- (b) producing renewable hydrogen from the received combustible fluid feedstock;
- (c) producing liquid transportation or heating fuel in a process comprising combining renewable hydrogen with crude oil derived liquid hydrocarbons under conditions to hydrogenate the liquid hydrocarbons;
- (d) generating or receiving numerical information relating to a product selected from (i) combustible fluid feedstock derived from biogas; (ii) renewable hydrogen; (iii) a transportation or heating fuel comprising renewable hydrogen; and (iv) crude biogas, the numerical information comprising information representing at least 3 parameters selected from:
  - (i') the type of product that is made by a producer or importer of the product;
  - (ii') year in which the product was produced;
  - (iii') a registration number associated with the producer or importer of the product; and
  - (iv') a serial number associated with a batch of the product; and (e) providing the numerical information generated or received in step (d) from a producer or purchaser of the product to a government regulatory agency.

20. The method of claim 19, wherein the product is combustible fluid feedstock derived from biogas or crude biogas.

21. The method of claim 19, wherein the numerical information is a RIN.

22. The method of claim 19, further comprising generating an LCFS credit relating to the product of step (d).

23. The method of claim 19, wherein the renewable hydrogen is combined with the crude oil derived liquid hydrocarbon in a hydrocracker operation or reactor.

24. The method of claim 19, wherein a liquid transportation fuel is produced in step (c).

25. A method of producing a combustible fluid feedstock for use in producing a transportation or heating fuel, said method comprising:
（a) producing a combustible fluid feedstock by a process comprising:
 (i) converting waste organic material to crude biogas using microorganisms;
 (ii) collecting an amount of crude biogas using an apparatus; and
 (ii) removing impurities from the crude biogas to yield a combustible fluid feedstock;
(b) arranging for a fuel production facility to receive combustible fluid feedstock to use in a process for making liquid transportation or heating fuel, wherein said process comprises combining renewable hydrogen derived from the combustible fluid feedstock with crude oil derived liquid hydrocarbons under conditions to hydrogenate the liquid hydrocarbons;
(c) generating numerical information relating to the combustible fluid feedstock or crude biogas, said information comprising information representing at least 3 parameters selected from:
 (i') the type of renewable fuel that it is;
 (ii') year in which the combustible fluid feedstock was produced;
 (iii') a registration number associated with the producer or importer of the combustible fluid feedstock; and
 (iv') a serial number associated with a batch of the combustible fluid feedstock; and
(d) providing the numerical information relating to the combustible fluid feedstock or crude biogas to a government regulatory agency and to the fuel production facility in step (b).

26. The method of claim 25, wherein the crude oil derived liquid hydrocarbons are desulfurized.

27. The method of claim 25, wherein the numerical information is a RIN.

28. The method of claim 27, further comprising generating an LCFS credit relating to the combustible fluid feedstock.

29. The method of claim 25, wherein the renewable hydrogen is combined with the crude oil derived liquid hydrocarbon in a hydrocracker operation or reactor.

30. The method of claim 25, wherein in step (b) the fuel production facility is a transportation fuel production facility that receives the combustible fluid feedstock for use in making liquid transportation fuel.

31. A method for generating a renewable fuel credit associated with biogas produced from waste organic material, said method comprising:
(a) producing biogas derived combustible fluid feedstock from biogas;
(b) arranging for a fuel production facility to buy combustible fluid feedstock to make renewable hydrogen for use in a process for making liquid transportation or heating fuel, wherein said process comprises combining renewable hydrogen with crude oil derived liquid hydrocarbons to hydrogenate the liquid hydrocarbons;
(c) generating a RIN associated with the biogas;
(d) introducing a first amount of the biogas derived combustible fluid feedstock to apparatus for delivering a combustible fluid feedstock to a fuel production facility; and
(e) transferring a RIN associated with biogas to a purchaser of the biogas.

32. The method of claim 31, wherein in step (b) the fuel production facility is a transportation fuel production facility that buys the combustible fluid feedstock for use in making liquid transportation fuel.

33. A method of transforming waste organic material to produce a liquid transportation or heating fuel comprising:
(a) subjecting waste organic material to anaerobic digestion by microorganisms in a biogas production facility that incorporates apparatus to collect the microbially generated biogas;
(b) collecting an amount of crude biogas from the biogas production facility;
(c) removing impurities from the crude biogas to yield a combustible fluid feedstock;
(d) introducing a first amount of the combustible fluid feedstock from step (b) or (c) to apparatus for delivering a combustible fluid feedstock to fuel production facility;
(e) generating or receiving numerical information relating to a product selected from (i) combustible fluid feedstock derived from crude biogas; (ii) renewable hydrogen; (iii) a transportation or heating fuel comprising renewable hydrogen; or (iv) crude biogas, the numerical information comprising information representing at least 3 parameters selected from:
 (i') the type of product that is made by the producer or importer of the product;
 (ii') year in which the product was produced;
 (iii') a registration number associated with the producer or importer of the product; and
 (iv') a serial number associated with a batch of the product;
(f) withdrawing for use at a fuel production facility a second amount of combustible fluid feedstock approximately equal to the first amount of combustible fluid feedstock;
(g) processing at the fuel production facility the second amount of combustible fluid feedstock to produce renewable hydrogen;
(h) producing a third amount of liquid transportation or heating fuel by a process that comprises combining renewable hydrogen derived from the second amount of combustible fluid feedstock with a crude oil derived liquid hydrocarbon; and
(i) providing the numerical information generated or received in step (e) to a government regulatory agency.

34. The process of claim 33, wherein the renewable hydrogen is combined with the crude oil derived liquid hydrocarbon in a reactor under conditions to hydrogenate the liquid hydrocarbon with the renewable hydrogen.

35. The process of claim 34, wherein the reactor is a hydrotreater.

36. The method of claim 33, wherein the transportation or heating fuel is selected from gasoline, diesel, heating oil and jet fuel.

37. The method of claim 33, wherein a liquid transportation fuel is produced in step (h).

38. A method of producing a transportation or heating fuel comprising:
(a) causing a first amount of combustible fluid feedstock to be introduced to apparatus capable of delivering a combustible fluid feedstock to a fuel production facility, said first amount of combustible fluid feedstock being derived from a crude biogas from which impurities were removed following collection from a biogas production facility;
(b) generating or receiving numerical information relating to a product selected from (i) combustible fluid feedstock derived from crude biogas; (ii) renewable hydrogen; (iii) a transportation or heating fuel comprising renewable hydrogen; and (iv) crude biogas, the numerical information comprising information representing at least 3 parameters selected from:
(i') the type of product that is made by a producer or importer of the product;
(ii') year in which the product was produced;
(iii') a registration number associated with the producer or importer of the product; and
(iv') a serial number associated with a batch of the product;
(c) withdrawing for use at a fuel production facility, a second amount of combustible fluid feedstock approximately equal to the first amount of combustible fluid feedstock;
(d) processing at the fuel production facility the second amount of combustible fluid feedstock to produce renewable hydrogen;
(e) producing a third amount of liquid transportation or heating fuel by a process that comprises combining renewable hydrogen derived from the second amount of combustible fluid feedstock with a crude oil derived liquid hydrocarbon; and
(f) providing numerical information generated or received in step (b) to a government regulatory agency.

39. The process of claim 38, wherein the renewable hydrogen is combined with the crude oil derived liquid hydrocarbon in a reactor under conditions to hydrogenate the liquid hydrocarbon with the renewable hydrogen.

40. The process of claim 38, wherein the reactor is a hydrocracker.

41. The method of claim 38, wherein the transportation or heating fuel is selected from gasoline, diesel, heating oil and jet fuel.

42. The method of claim 38, wherein the product in step (b) is combustible fluid feedstock derived from biogas or crude biogas.

43. The method of claim 38, wherein a liquid transportation fuel is produced in step (e).

44. A method of producing a combustible fluid feedstock for use in producing a partially renewable transportation or heating fuel, said method comprising:
(a) producing or receiving combustible fluid feedstock derived from biogas that has been produced from waste organic material;
(b) introducing a first amount of the combustible fluid feedstock from step (a) to apparatus for delivering a combustible fluid feedstock to fuel production facility; and
(c) causing a fuel production facility to use combustible fluid feedstock in a process that produces transportation or heating fuel from a crude oil derived hydrocarbon, said process comprising:
withdrawing a second amount of combustible fluid feedstock from the apparatus approximately equal to the first amount of combustible fluid feedstock;
(d) generating numerical information relating to the first amount of combustible fluid feedstock comprising information representing at least 3 parameters selected from:
(i) the type of renewable fuel that it is;
(ii) year in which the combustible fluid feedstock was produced;
(iii) a registration number associated with the producer or importer of the combustible fluid feedstock; and
(iv) a serial number associated with a batch of the combustible fluid feedstock; and
(e) providing the numerical information relating to the first amount of combustible fluid to a government regulatory agency and a purchaser of the combustible fluid feedstock.

45. The method of claim 44, wherein the transportation or heating fuel is selected from gasoline, diesel, heating oil and jet fuel.

46. The method of claim 44, wherein the combustible fluid feedstock in step (a) is produced by a biogas production facility selected from a landfill, a waste treatment facility or a manure digestion facility.

47. The method of claim 44, wherein the fuel production facility processes the second amount of combustible fluid feedstock to produce renewable hydrogen.

48. The process of claim 44, wherein the renewable hydrogen is combined with the crude oil derived liquid hydrocarbon in a reactor under conditions to hydrogenate the liquid hydrocarbon with the renewable hydrogen.

49. The process of claim 48, wherein the reactor is a hydrocracker.

50. The process of claim 48, wherein the crude oil derived liquid hydrocarbon is desulfurized.

51. The method of claim 44, wherein the numerical information is a RIN.

52. The process of claim 44, further comprising generating an LCFS credit.

53. The method of claim 44, wherein in step (c) the fuel production facility is a transportation fuel production facility that uses the combustible fluid feedstock for making liquid transportation fuel.

* * * * *